(12) United States Patent
Yu et al.

(10) Patent No.: US 8,194,514 B2
(45) Date of Patent: Jun. 5, 2012

(54) METHODS FOR ASSESSING THE RESULTS OF DISC-BASED BIOASSAYS WITH STANDARD COMPUTER OPTICAL DRIVES

(75) Inventors: Hua-Zhong (Hogan) Yu, Burnaby (CA); Yunchao Li, Burnaby (CA); Miao-Ling (Lily) Ou, Coquitlam (CA)

(73) Assignee: Simon Fraser University, Burnaby, British Columbia (CA)

(*) Notice: Subject to any disclaimer, the term of this patent is extended or adjusted under 35 U.S.C. 154(b) by 16 days.

(21) Appl. No.: 12/920,100

(22) PCT Filed: Mar. 2, 2009

(86) PCT No.: PCT/CA2009/000223
§ 371 (c)(1),
(2), (4) Date: Dec. 6, 2010

(87) PCT Pub. No.: WO2009/105877
PCT Pub. Date: Sep. 3, 2009

(65) Prior Publication Data
US 2011/0103212 A1 May 5, 2011

Related U.S. Application Data

(60) Provisional application No. 61/032,787, filed on Feb. 29, 2008.

(51) Int. Cl.
*G11B 7/00* (2006.01)
(52) U.S. Cl. .................... 369/53.15; 369/126
(58) Field of Classification Search ............. 369/53.12, 369/53.14, 53.15, 53.17, 53.27, 126; 435/6.15, 435/24.32, 24.3
See application file for complete search history.

(56) References Cited

U.S. PATENT DOCUMENTS 7,429,454 B2 * 9/2008 Mettus et al. ................ 435/6.15
2002/0106661 A1 8/2002 Virtanen

OTHER PUBLICATIONS

La Clair, J.J. et al., 'Molecular screening on a compact disc' Org. Biomol. Chem. (2003) 1(18): 3244-3249.
Lange, S.A. et al., 'Measuring biomolecular binding events with a compact disc player device' Angew. Chem. Int. Ed. (2006) 45(2): 270-273.

(Continued)

*Primary Examiner* — Nabil Hindi
(74) *Attorney, Agent, or Firm* — Chernoff Vilhauer McClung & Stenzel, LLP

(57) ABSTRACT

Methods and systems are described for assessing the results of a bioassay between probe biomolecules and target biomolecules using conventional optical disk drive. particular methods involve: bonding the probe biomolecules to a polycarbonate (PC) surface of an optical disk having digital data comprising error-detection redundancies recorded thereon: introducing the target biomolecules to the PC surface of the optical disk in a vicinity of the bonded probe biomolecules; processing the bioassay to alter a manner in which a read light from the optical disk interacts optically with the optical disk in a vicinity of positive bioassay results where the target biomolecules have bonded to the probe biomolecules; reading the digital data from the optical disk using the optical drive and using the error-redundancies to detect errors in the digital data read by the optical drive; mapping the detected errors to corresponding locations on the optical disk; and determining that positive bioassay results have occurred at the locations of the detected errors.

73 Claims, 10 Drawing Sheets

OTHER PUBLICATIONS

Li, Y. et al., 'Digitized molecular diagnostics: reading disk-based bioassays with standard computer drives' Anal. Chem. (2008) 80(21): 8216-8223.

Yu, H. Z., New chemistry on old CDs, Chem. Commun. 2633-2636 (2004).

Kido, H. et al., Disc-based immunoassay microarrays, Anal. Chim. Acta. 411, 1-11 (2000).

McCarley, R. L. et al., Resist-free patterning of surface architectures in polymer-based microanalytical devices, J. Am. Chem. Soc. 127, 842-843 (2005).

Morais, S. et al., DNA microarraying on compact disc surfaces. Application to the analysis of single nucleotide polymorphisms in Plum pox virus, Chem. Commun. 22, 2368-2370 (2006).

Li, Y. C. et al. DNA detection on plastic: Surface activation protocol to convert polycarbonate substrates to biochip platforms, Anal. Chem. 79, 426-433 (2007).

Madou, M. J. et al. Design and fabrication of CD-like microfluidic platforms for diagnostics: Microfluidic functions, Biomedical Microdevices 3, 245-254 (2001).

Madou, M. et al. Lab on a CD, Annu. Rev. Biomed. Eng. 8, 601-628 (2006).

Alexandre, I. et al., Compact disc with both numeric and genomic information as DNA microarray platform, BioTechniques 33, 435-439 (2002).

Barathur, R. et al., New disc-based technologies for diagnostic and research applications, Psychiatric Genetics 12, 193-206 (2002).

Potyrailo, R. A. et al., Analog signal acquisition from computer optical disk drives for quantitative chemical sensing, Anal. Chem. 78, 5893-5899 (2006).

Bauls et al., PMMA isocyanate-modified digital discs as a support for oligonucleotide-based assays, Bioconjugate Chem. 18, 1408-1414 (2007).

Morais, S. et al., Microimmunoanalysis on standard compact discs to determine low abundant compounds, Anal. Chem. 79, 7628-7635 (2007).

Jones, C. L., Cryptographic hash functions and CD-based optical biosensors, Problem. Nonlinear Anal. Eng. Syst. 11, 17-36 (2005).

Lane, P. M. et al., Compact disc players in the laboratory: Experiments in optical storage, error correction, and optical fiber communication, IEEE Transactions on Education 44, 47-60 (2001).

Pohlmann, K. C., The compact disc handbook, A-R Editions Inc., Madison, 1992.

kprobe (available from http://www.k-probe.com/).

Nero™ CD-DVD Speed (available from http://cdspeed2000.com/).

\* cited by examiner

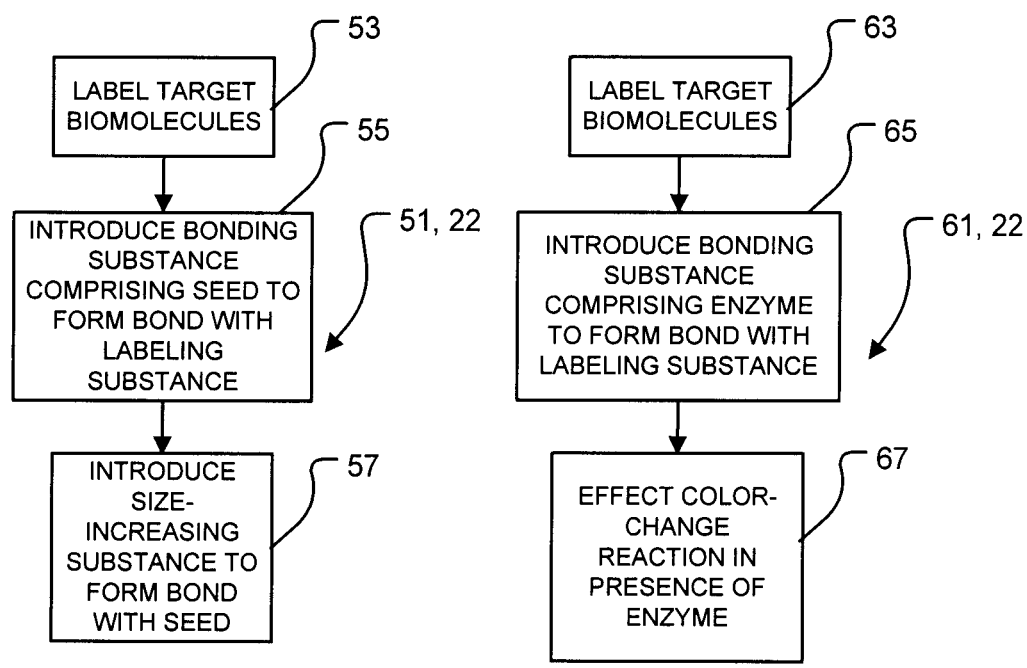

MANUFACTURED AUDIO CD  AUDIO DATA RECORDED ON CD-R

METHODS FOR ASSESSING THE RESULTS OF DISC-BASED BIOASSAYS WITH STANDARD COMPUTER OPTICAL DRIVES

RELATED APPLICATIONS

This application claims the benefit of the priority of U.S. application No. 61/032,787 entitled METHODS FOR ASSESSING THE RESULTS OF DISC-BASED BIOASSAYS WITH STANDARD COMPUTER OPTICAL DRIVES filed 29 Feb. 2008 (the "Provisional Application"), which is hereby incorporated herein by reference. For the purposes of the United States, this application claims the benefit of the Provisional Application under 35 USC §119.

This application contains content related to the content of U.S. application Ser. No. 12/006,072 entitled SURFACE ACTIVATION METHODS FOR POLYMERIC SUBSTRATES TO PROVIDE BIOCHIP PLATFORMS AND METHODS FOR DETECTION OF BIOMOLECULES THEREON filed 28 Dec. 2007 (the "Surface Activation Application"), which is hereby incorporated herein by reference.

TECHNICAL FIELD

This invention relates to the field of molecular diagnostics. Particular embodiments provide methods and systems for assessing the results of disc-based bioassays with standard computer optical drives.

BACKGROUND

Biomolecular screening (e.g. using microarray technology) is a useful technology for high-throughput analysis of specific interactions between biological macromolecules (e.g. DNA, proteins, carbohydrates or the like). However, the ability to use microarray technology for various applications (e.g. gene profiling, clinical diagnosis, immunoassays, drug discovery or the like) is currently typically limited to well-funded biomedical laboratories or hospital settings which are equipped with relatively expensive equipment (e.g. robotic spotters, laser fluorescence scanners and the like). Accordingly, there is a general need for cost-effective techniques for implementing biomolecular screening processes.

Optical discs (e.g. compact discs (CDs), digital video discs (DVDs) and the like) comprising polycarbonate (PC) have recently been proposed as alternative substrates to glass slides/silicon wafers for the preparation of microarrays—see, for example, Yu, H. Z., New chemistry on old CDs, *Chem. Commun.* 2633-2636 (2004); Kido, H. et al., Disc-based immunoassay microarrays, *Anal. Chim. Acta.* 411, 1-11 (2000); McCarley, R. L. et al., Resist-free patterning of surface architectures in polymer-based microanalytical devices, *J. Am. Chem. Soc.* 127, 842-843 (2005); Morais, S. et al., DNA microarraying on compact disc surfaces. Application to the analysis of single nucleotide polymorphisms in Plum pox virus, *Chem. Commun.* 22, 2368-2370 (2006); and Li, Y. C. et al. DNA detection on plastic: Surface activation protocol to convert polycarbonate substrates to biochip platforms, *Anal. Chem.* 79, 426-433 (2007). Microfluidic techniques have been proposed for use with PC optical disc substrates to control the transfer of fluid to the optical disc surface by disc spinning—see, for example, Madou, M. J. et al. Design and fabrication of CD-like microfluidic platforms for diagnostics: Microfluidic functions, *Biomedical Microdevices* 3, 245-254 (2001); and Madou, M. et al. Lab on a CD, *Annu. Rev. Biomed. Eng.* 8, 601-628 (2006).

Recent research has attempted to adapt or modify computer optical drives (e.g. CD drives, DVD drives or the like) for use as optical readout devices for microarray-based biochips. However, most of such research has required comprehensive hardware modification to commercially available optical drives—see, for example, Alexandre, I. et al., Compact disc with both numeric and genomic information as DNA microarray platform, *BioTechniques* 33, 435-439 (2002); Barathur, R. et al., New disc-based technologies for diagnostic and research applications, *Psychiatric Genetics* 12, 193-206 (2002); Lange, S. A. et al., Measuring biomolecular binding events with a compact disc player device, *Angew. Chem. Int. Ed.* 45, 270-273 (2006); Potyrailo, R. A. et al., Analog signal acquisition from computer optical disk drives for quantitative chemical sensing, *Anal. Chem.* 78, 5893-5899 (2006); Manorais, S. et al., PMMA isocyanate-modified digital discs as a support for oligonucleotide-based assays, *Bioconjugate Chem.* 18, 1408-1414 (2007); and Morais, S. et al., Microimmunoanalysis on standard compact discs to determine low abundant compounds, *Anal. Chem.* 79, 7628-7635 (2007). The need to modify commercially available optical drives for use in assessing the results of disc-based bioassays is inconvenient, time consuming and expensive.

Other researchers have developed "software" techniques for employing optical drives to assess the results of disc-based bioassays. These techniques generally involve analyzing the digital signals received from optical drives—see, for example, La Clair, J. J. et al. Molecular screening on a compact disc, *Org. Biomol. Chem.* 1, 3244-3249 (2003); and Jones, C. L., Cryptographic hash functions and CD-based optical biosensors, *Problem. Nonlinear Anal. Eng. Syst.* 11, 17-36 (2005). The La Clair technique involves activation of a CD-R surface for attaching ligand molecules via phosphorylation in acetonitrile, which is practically difficult because of the incompatibility of PC with organic solvents. Also, the proposed La Clair readout protocol is technically challenging as the tested proteins are not typically large enough to be detectable by an optical drive. The Jones technique involves observing stained bacterial cells which have been physically absorbed on disc using an optical disc drive in the place of a conventional microscope. The size of the Jones bacterial cells is typically on an order of a few microns to tens of microns.

There remains a general desire for methods for using conventional computer optical drives as devices for assessing the results of biomolecular screening processes (e.g. microarray-based bioassays) carried out on the PC substrates of optical discs.

SUMMARY

One aspect of the invention provides a method for assessing bioassay results using a conventional (i.e. non-modified) optical disc drive. Data incorporating error detection redundancy is recorded or otherwise provided on an optical disc. Such data may comprise audio data on a CD or video data on a DVD or Blu-Ray disc, for example. The polycarbonate (PC) surface of the optical disc is activated, so as to more readily accept (e.g. by chemical bonding) desired biomolecules. By way of non-limiting example, the PC surface of the optical disc may be activated using a combination of ozone and UV irradiation as described in the Surface Activation Application. Such activation may promote the formation of carboxylic acid groups (COOH) on the PC surface. In some embodiments, depending on the probe biomolecules to be bonded to the PC surface, the PC surface of the optical disc may be treated with other chemical and/or physical treatments that promote the bonding of the probe biomolecules to the PC surface. By way of non-limiting example, such chemical treatments may promote the binding of the probe biomolecules to the COOH groups on the activated PC surface. A bioassay is then prepared on the optical disc.

The bioassay may be processed to make positive bioassay results more easily detectable in an optical drive. In particular embodiments, such processing may involve increasing the size of the sites of positive assay results to change the amount of light scattered from the positive bioassay results and/or creating a color change or otherwise selectively introducing a colored material in a vicinity of the sites of positive assay results, such that the colored material changes the light absorption properties in the vicinity of the sites of the positive bioassay results.

Increasing the size of positive assay result sites may involve labeling target bioassay biomolecules with a labeling substance (e.g. biotin or thiol). The labeling substance may be reactive with a bonding substance (e.g. streptavidin). The bonding substance may comprise or may form a conjugate with a metal seed (e.g. gold). Further size increasing processing may comprise introducing other metal(s) (e.g. silver) which bond to the metal seed, thereby increasing the size of the positive assay result site.

Creating a color change or selectively introducing a colored material in a vicinity of the sites of positive assay results may involve labeling target bioassay biomolecules with a labeling substance (e.g. biotin), introducing a bonding substance which bonds to the labeling substance and which comprises an enzyme for catalyzing a color-change reaction and subsequently effecting a color-change reaction by introducing the reactants to a color-change reaction, such that the color-change reaction selectively takes place in locations where the enzyme is present. Such color-change reactions may induce a precipitate which may have a different color, for example.

In other embodiments, probe biomolecules may be processed (e.g. by increasing the size of or changing the color) to make negative assay results more easily readable. Processes similar to those described herein for use with positive assay results (e.g. for target biomolecules) may be tailored for use with negative assay results (e.g. for probe biomolecules).

After processing, the optical disc is read in an optical drive. A computer or similarly configured processor executing suitable error mapping and data decoding software attempts to read the data recorded on the disc. Upon data decoding, errors are detected in data corresponding to the locations of processed bioassay results (e.g. positive assay results or negative assay results, as the case may be). The location of errors within the data may be mapped by error mapping software to physical locations on the optical discs, thereby identifying particular bioassay sites having positive or negative assay results.

Further aspects of the invention, further features of specific embodiments of the invention and applications of the invention are described below.

BRIEF DESCRIPTION OF DRAWINGS

In drawings which show non-limiting embodiments of the invention:

FIG. 1A is a schematic block diagram of a method for increasing the size of the site of a positive assay result which may be used to implement the signal enhancing processing of the method of FIG. 1;

FIG. 1B is a schematic block diagram of a method for changing the color of a substance in a vicinity of the site of a positive assay result which may be used to implement the signal enhancing processing of the method of FIG. 1;

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the disclosure. Accordingly, the specification and drawings are to be regarded in an illustrative, rather than a restrictive, sense.

Figure 1:
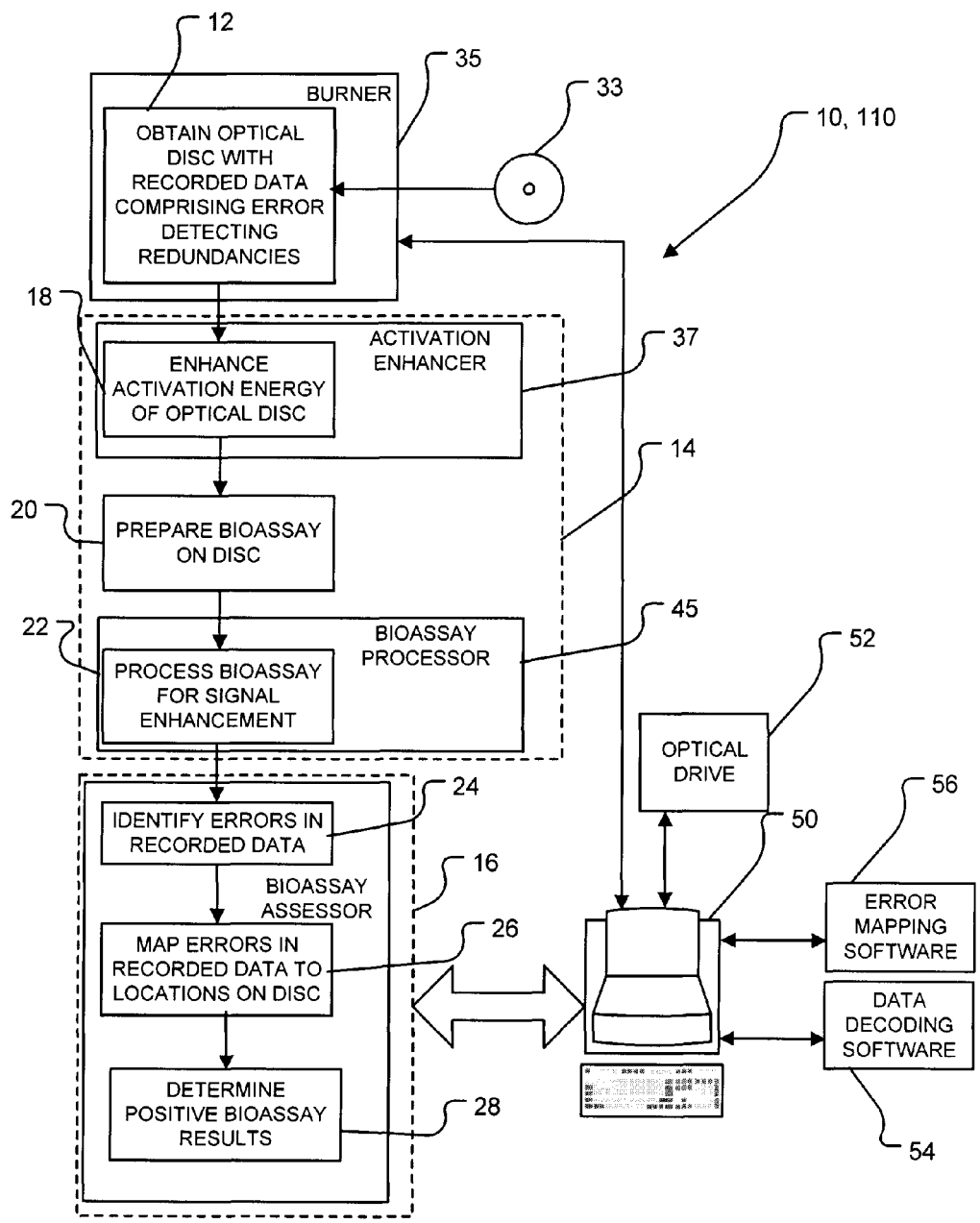
FIG. 1 is a schematic block diagram depiction of a method for preparing a bioassay on an optical disc and assessing the results of the bioassay using an optical disc drive.

FIG. 1 schematically depicts a block diagram representation of a method 10 and a system 110 for preparing a bioassay on an optical disc 33 and assessing the bioassay results using a conventional optical disc drive 52. In the illustrated embodiment, system 110 includes a computer 50, which is connected to operate optical drive 52 and which is configured to run error mapping software 56 and data decoding software 54 (described in more detail below). In some embodiments, computer 50 may comprise a conventional personal computer (PC) operating a conventional operating system (e.g. Windows™, Mac OS™, Unix™ or unix-like operating systems). In other embodiments, computer 50 may comprise one or more suitably programmed processor(s) together with suitable hardware configured to perform the functions of computer 50 described herein. In some embodiments, portions of decoding software 54 and/or error mapping software 56 (or their respective functions) may be executed (performed) by data processors which are local to optical drive 52. In such embodiments, computer 50 may not be required.

Optical disc drive 52 is a conventional optical disc drive configured to use laser light and/or electromagnetic energy near the light spectrum to read digital data from an optical disc (e.g. optical disc 33) and connected to provide digital data read from the optical disc to computer 50. By way of non-limiting example, optical disc drive 52 may comprise a compact disc (CD) drive, a digital video disc (DVD) drive, a Blu-Ray disc drive or a combination drive, capable reading digital data from multiple types of optical discs. In some embodiments, optical disc drive 52 is also configured to record digital data onto optical discs (e.g. optical disc 33). Recording of digital data onto optical discs is also referred to as "writing" or "burning" the digital data onto the optical discs. Optical disc drives and their operation to read digital data from and/or to write digital data to optical discs are known to those skilled in the art.

Method 10 commences in block 12 which comprises obtaining an optical disc 33 onto which digital data comprising error checking redundancies is recorded or otherwise imparted. Generally speaking, method 10 may be practiced using any suitable optical disc 33 which is capable of performing in accordance with the description set out below. Currently preferred optical discs comprise a layer of polycarbonate (PC) and may include, without limitation, compact discs (CDs), digital video discs (DVDs), Blu-ray discs or the like. In some embodiments, optical discs used in accordance with the invention may comprise layers of polymethylmethacrylate (PMMA), polystyrene (PS), and polydimethylsiloxane (PDMS) in addition to or in the place of PC.

In the illustrated embodiment, the digital data recorded onto optical disc 33 is recorded using an optical disc burner 35. In some embodiments, optical disc burner 35 may be implemented by optical disc drive 52, although this is not necessary and burner and disc drive 52 may be implemented by separate hardware devices. In some embodiments, burner 35 may operate under the control of computer 50 which may execute suitable burning software, although this too is not necessary, and the operation of burner 35 may be independently controlled (e.g. by a different computing device). In some embodiments, the recorded data on optical disc 33 may be recorded during fabrication of the disc (e.g. at a factory) prior to purchase of optical disc 33. The process of recording digital data onto an optical disc during fabrication may be referred to as "pressing" the disc.

The data recorded on optical disc 33 is encoded using error-detection redundancies—i.e. extra (redundant) data which are used to ascertain errors in the payload data. By way of non-limiting example, audio data recorded on conventional audio CDs is encoded with error correction redundancies in a process known as Cross Interleave Reed-Solomon Coding (CIRC) which incorporates one redundant parity byte for every three bytes of audio data payload—see Lane, P. M. et al., Compact disc players in the laboratory: Experiments in optical storage, error correction, and optical fiber communication, *IEEE Transactions on Education* 44, 47-60 (2001); and Pohlmann, K. C., *The compact disc handbook*, A-R Editions Inc., Madison, 1992, which are hereby incorporated herein by reference. A similar Reed-Solomon error correction encoding technique is used for DVD video encoding technology. Error correction techniques are also incorporated into the digital video data recorded onto Blu-ray discs.

While CD audio encoding technology and DVD video encoding technology based on CIRC or other similar encoding techniques incorporate error "correction" redundancy data, this is not necessary. In some embodiments, it is sufficient for the data recorded on the optical disc in block 12 to comprise error "detection" redundancy data, provided that it is possible, using suitably configured software (e.g. data decoding software 54 and error mapping software 56), to detect the location of errors within the data. The use of software to detect the location of errors is described in more detail below. Other non-limiting examples of error-detection redundancies which may be used in association with method 10 and system 110 include: data repetition schemes, data parity schemes, data checksum schemes, cyclic redundancy check schemes, horizontal redundancy check schemes, vertical redundancy check schemes, hamming distance-based schemes, hash function schemes, polarity schemes and cryptographic message-based schemes.

Once an optical disc 33 incorporating data with error-detecting redundancies is prepared or otherwise procured in block 12, method 10 proceeds to block 14 which involves preparing a bioassay on the optical disc in a format suitable for assessment using optical disc drive 52. In the illustrated embodiment, block 14 comprises several sub-blocks which are shown in block diagram format in FIG. 1 and in graphical format in FIG. 2A. Block 14 commences in sub-block 18, which involves enhancing the activation energy of optical disc 33, such that biomolecules may be more easily immobilized on the PC layer of optical disc 33. In some embodiments, sub-block 18 may involve washing the PC layer of disc 33 (e.g. with de-ionized water) to remove environmental contaminants and the like. In the illustrated embodiment, sub-block 18 is performed by an activation enhancer 37.

In currently preferred embodiments, the activation of optical disc 33 in sub-block 18 comprises irradiating optical disc 33 with ultra violet (UV) radiation in the presence of ozone ($O_3$), as described in the Surface Activation Application. In such embodiments, activation enhancer 37 may comprise a source of UV radiation (e.g. a UV lamp) and a source of ozone (e.g. the OZO-2VTT ozone generator sold by Ozomax, Inc. of Shefford, Quebec, Canada). In some embodiments, the ozone concentration in the vicinity of disc 33 when it is being irradiated with UV is greater than 10 ppm. In some embodiments, this ozone concentration is greater than 20 ppm. The UV radiation intensity may be relatively low to avoid or minimize damaging the irradiated surface of disc 33. In particular embodiments, the UV radiation intensity is less than about 50 mW/cm$^2$. In other embodiments, this radiation intensity is less than about 20 mW/cm$^2$.

Figure 2A:
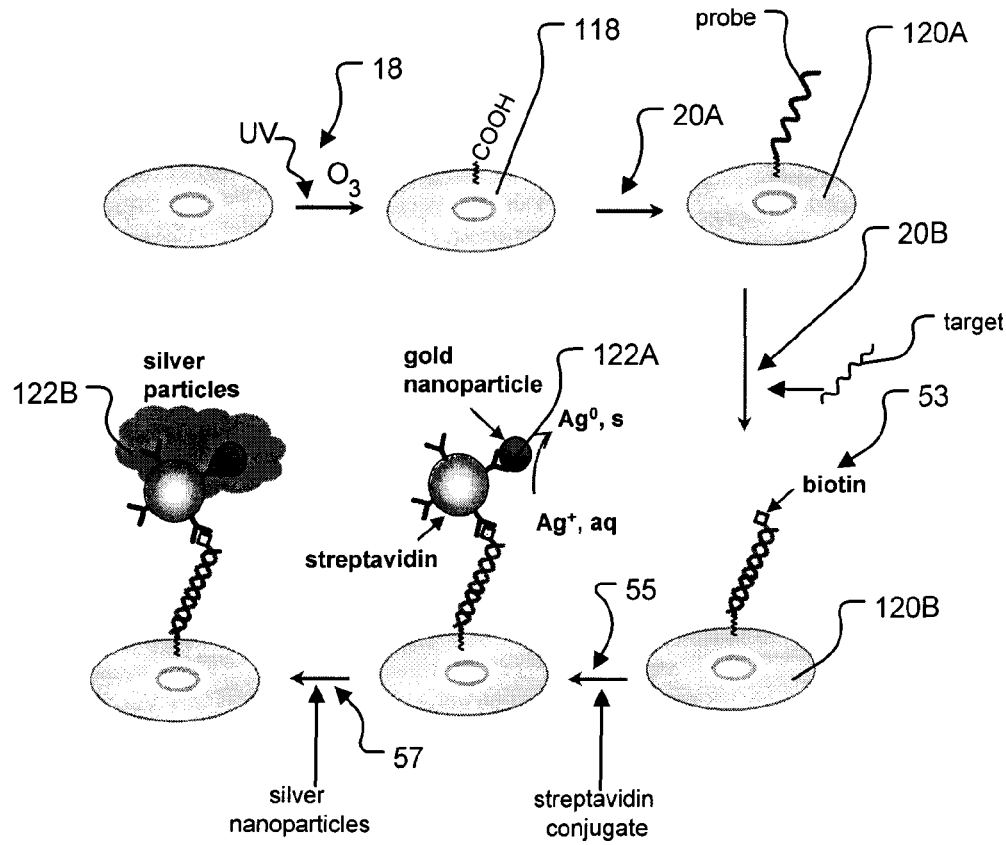
FIG. 2A is a schematic graphical depiction of a method for preparing a bioassay on an optical disc capable for assessment in an optical drive according to a particular embodiment of the invention.

As discussed in the Surface Activation Application, irradiating optical disc 33 with UV radiation in the presence of ozone is thought to cause a reaction which increases the hydrophilicity of the PC surface of optical disc 33 and results in the formation of carboxylic acid groups (COOH) on the PC surface as shown at 118 (FIG. 2A). Without wishing to be bound by theory, PC is known to undergo a photo-Fries reaction under irradiation at certain wavelengths (e.g. wavelengths in a range between 254-300 nm) resulting in the formation of phenyl salicylates and hydroxybenzophenones. The presence of ozone may induce the formation of an O2-contact charge transfer complex (an adduct), which is the initial step in the photo-oxidation of aliphatic and aromatic alkenes. Together, the UV radiation and the ozone are thought to cause the formation of an adduct which is then thought to reassemble itself to form a carboxylic group via a series of hydriperoxide intermediates. Carboxylic acid groups (COOH) formed on the PC surface of disc 33 are receptive to forming bonds with biomolecules and permit immobilization of biomolecules on optical disc 33. In particular embodiments, biomolecules may be immobilized on activated optical disc 33 by covalent coupling. In one particular non-limiting example embodiment, covalent amide coupling may facilitate bonding between amino ($NH_2$) groups on particular biomolecules to carboxylic acid (COOH) groups on the activated PC surface.

In particular embodiments, activation enhancer 37 uses UV radiation both to create ozone from molecular $O_2$ present at the reaction site (e.g. by photolysis of molecular $O_2$) and to irradiate the PC surface of disc 33. Such UV radiation may be provided at different wavelengths (i.e. one wavelength that tends to promote the formation of ozone from molecular $O_2$ and a second wavelength that tends to promote the activation reaction at the PC surface of disc 33). Surface activation itself is not easily measurable. However, when the PC surface of disc 33 is activated, it becomes relatively hydrophilic resulting in a decrease in the magnitude of its water contact angle.

In some embodiments, depending on the biomolecules and/or the bonding sites of the biomolecules involved in the bioassay (e.g. the probe biomolecules to be bonded to the PC surface), the PC surface of the optical disc may optionally be further activated by treating the optical disc with chemical and/or physical treatments that promote the bonding of the biomolecules to the PC surface. Such chemical and/or physical treatments may promote the bonding of certain bonding sites of biomolecules to the carboxylic acid (COOH) groups on the activated PC surface. In one particular non-limiting example, where it is desired to covalently bond amino ($NH_2$) groups of biomolecules to the carboxylic acid (COOH) groups on the PC surface, optical disc 33 may be treated with 1-ethyl-3-(3'-dimethylaminopropyl)-carbodiimide (EDC) and/or N-hydroxysuccinimide (NHS). Since EDC and NHS are relatively inexpensive, optical disc 33 (or at least its PC surface) may be completely coated or immersed in these substances. Treatment with other chemicals may promote other types of bonds between bonding sites of biomolecules involved in the bioassay and the PC surface of optical disc 33. In the illustrated embodiment, activation of optical disc 33 (including optional bond-promoting chemical treatment) takes place in block 18 before preparing the bioassay on disc 33 in block 20. In other embodiments, optional bond-promoting chemical treatment may take place at the same time as the bioassay is prepared (e.g. by applying the chemical treatment to disc 33 along with one or more of the biomolecules involved in the bioassay).

Once the surface of optical disc 33 is activated in sub-block 18, method 10 proceeds to sub-block 20 which involves preparing a bioassay on activated optical disc 33. Sub-block 20 may itself comprise a multiple step process which is shown in more detail in FIG. 2A. Sub-block 20 may comprise immobilizing a first (probe) biomolecule on the activated PC surface of disc 33 (procedure 20A of FIG. 2A) and then exposing the immobilized probe biomolecule on disc 33 to a second (target) biomolecule in attempt to promote a reaction (e.g. a bonding reaction) between the probe and target biomolecules (procedure 20B of FIG. 2A). In this description and the accompanying claims, the term biomolecule is used to describe the reactants of the sub-block 20 bioassay formation process as a matter of convenience only and while the reactants of the sub-block 20 bioassay formation process may comprise molecules, these reactants are not specifically restricted to molecules and may comprise reactants of any suitable form, including, without limitation: molecules, clusters of molecules, nanoparticles, microparticles, cells, organisms or the like. Unless otherwise specified, the term biomolecules as used herein should be understood to incorporate any such reactants.

In the illustrated example embodiment of FIG. 2A, the sub-block 20 bioassay is a DNA bioassay where immobilization process 20A comprises immobilizing a DNA probe on the surface of activated optical disc 33 (as shown at 120A) and bonding process 20B comprises introducing target DNA into the vicinity of optical disc 33, such that the target DNA may bond to the DNA probe if the probe and target are matched. In the FIG. 2A example, the target DNA is shown as bonding to the probe DNA at 120B. In a typical bioassay process, one or more characteristics of the probe DNA are known and corresponding characteristics of the target DNA are unknown. If a bond is formed between the target DNA and the probe DNA, it is possible to deduce certain characteristics of the target DNA.

In general, the sub-bock 20 bioassay preparation procedure may comprise the preparation of any suitable bioassays. By way of non-limiting example, in some embodiments, the sub-block 120 bioassays formed from the first and second biomolecules may comprise: DNA bioassays; protein bioassays (e.g. where one or both of the probe and target biomolecules comprise proteins, such as biotin-streptavidin assays); immunoassays (e.g. where the probe and target biomolecules comprises antibodies and antigens, such as IgG-anti-IgG assays), carbohydrate/cell assays (e.g. where the probe and target biomolecules comprise a carbohydrate and a biological cell), assays involving aptamers (e.g. nucleic acid receptors), so-called "sandwich" assays (involving three or more reactants) and the like. The circumstance where the second (target) biomolecule of an assay bonds to the first (probe) biomolecule immobilized on the surface of optical disc 33 may be referred to as a "positive assay result" and the circumstance where the target biomolecule does not bond to the probe biomolecule may be referred to as a "negative assay result".

Figure 2E:
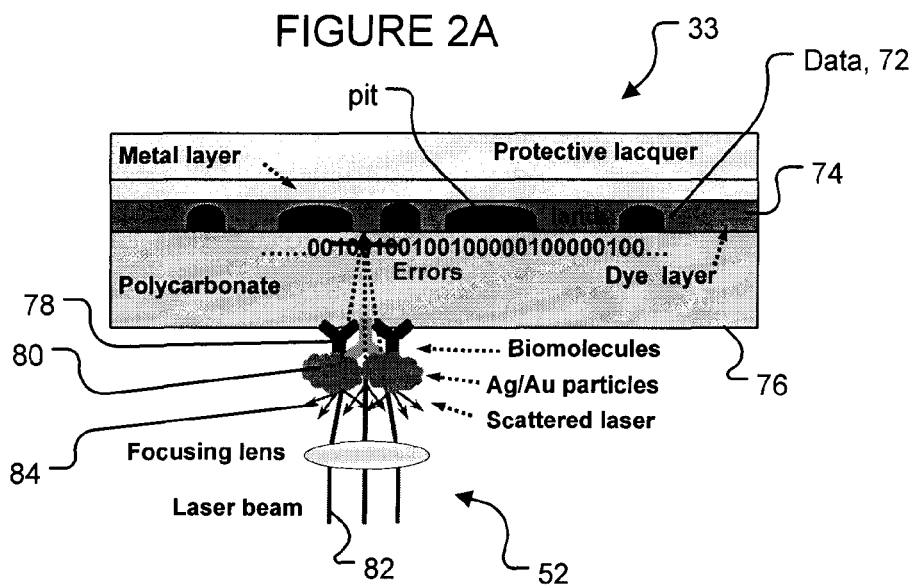
FIG. 2E is a schematic depiction of how biomolecule/nanoparticle conjugates formed on the PC surface of an optical disc block the reading laser of an optical disc drive and thereby generate errors.
Figure 2B:
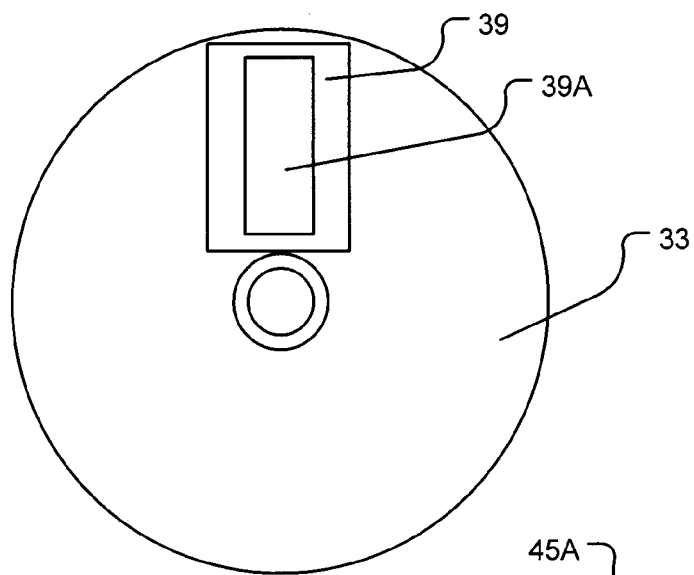
FIGS. 2B-2D show how fluidic channel plates may be used to prepare bioassays on the PC surface of an activated optical disc according to a particular embodiment of the invention.
Figure 2C:
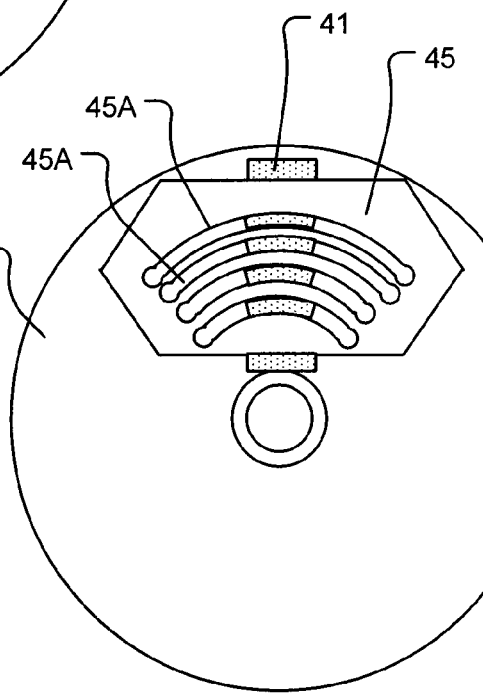
Figure 2D:
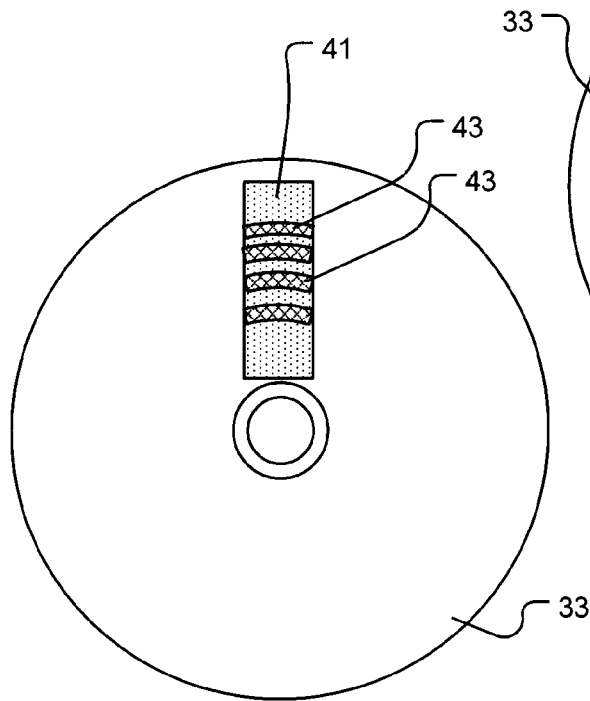

Preparation of the bioassay in sub-block 20 may comprise fluidic techniques for controlling the location of the immobilization and/or bonding reactions on the PC surface of optical disc 33. A particular example involving the use of fluidic channel plates 39, 45 is shown in FIGS. 2B-2D. The use of fluidic channel plates 39, 45 to prepare bioassays is described in the Surface Activation Application. Fluidic channel plates 39, 45 may be fabricated from polydimethylsiloxane (PDMS) or other suitable materials. Channel plates 39, 45 may be used to deliver the probe and target biomolecules to the surface of optical disc 33 in a spatial array format at specific location(s).

In the illustrated embodiment, channel plate 39 comprise a single channel 39A that is relatively wide. Channel plate 39 may be placed on the PC surface of disc 33 (FIG. 2B), whereupon a solution containing probe biomolecules may be introduced to channel 39A. In the illustrated embodiment, where channel 39A is sufficiently large to be visible to the eye, a sufficient amount of a buffer solution containing probe biomolecules may be added to fill channel 39A (i.e. to coat the PC surface of disc 33 in the region of channel 39A). Once the probe biomolecules within channel 39A bond to the surface of disc 33, channel plate 39 may be removed from optical disc 33 to leave a bonding strip 41 where the probe molecules have bonded to the PC surface.

A second fluidic channel plate 45 may then be placed on the surface of disc 33 (FIG. 2C). In the illustrated embodiment, channel plate 45 is a microfluidic channel plate which comprises a plurality of curved microfluidic channels 45A. In particular embodiments, the curvature of microfluidic channels 45A may be shaped concentrically and channel plate 45 may be located such that the centers of curvature of channels 45A coincide with the center of optical disc 33. At least a portion of one of more of channels 45A overlaps bonding strip 41 formed by the probe molecules and channel plate 39. Using techniques known in the art, buffer solutions containing target biomolecules may be introduced to microchannels 45A and drawn therethrough, such that the target biomolecules may react with the probe biomolecules in regions where channels 45A overlap bonding strip 41. The intersection of bonding strip 41 and channels 45A containing the target biomolecules provides bioassay test sites 43 at particular locations on disc 33 (FIG. 2D).

The locations of channel plates 39, 45 on disc 33 and the locations of channels 39A, 45A within channel plates 39 may be determined with precision, so that the locations of test sites 43 are known on the surface of disc 33. It will be appreciated by those skilled in the art that the particular configurations of channel plates 39, 45 and channels 39A, 45A shown in FIGS. 2B-2D are exemplary in nature and that channel plates 39, 45 and channels 39A, 45A may have other configurations in other embodiments. In one particular embodiment, channel plate 39 comprises a plurality of channels 39A which may also be microchannels and which may be generally radially oriented (relative to disc 33).

Preparation of particular bioassays on the surface of disc 33 may involve other procedures, such as, without limitation: washing disc 33 with suitable solvents between the various steps of the bioassay preparation (e.g. after immobilizing the probe biomolecules on disc 33 or after exposing the immobilized probe biomolecules to the target biomolecules); passivating the surface of disc 33 after the immobilization of probe biomolecules thereon. Passivation reactions may involve reacting the activated surface of disc 33 with suitable small molecules (such as, by way of non-limiting example, a blocking buffer containing 150 mM NaCl, 0.8% bovine serum albumin (BSA), 0.1% gelatin, 0.05% Tween 20 and 0.05% $NaN_3$. Both washing and passivating the PC surface of optical disc 33 help to reduce non-specific adsorption which may otherwise corrupt the results of bioassay assessment (e.g. by leading to false positive determinations).

After preparing the bioassay in sub-block 20, method 10 proceeds to sub-block 22 which involves processing the bioassay to enhance the signal generated in optical drive 52. Bioassay processing in sub-block 22 may be performed by a bioassay processor 45. In some embodiments, the sub-block 22 processing may involve undergoing a chemical and/or physical reaction to increase the size of the sites of positive assay results (i.e. locations in test sites 43 where the target biomolecule has bonded to the probe biomolecule which is immobilized on the surface of optical disc 33). In particular embodiments, sub-block 22 may comprise increasing the size of positive assay results using an autometallography process. Increasing the size of the sites of positive bioassay results may disrupt the laser beam of optical drive 52 by scattering the laser light. In other embodiments, the sub-block 22 processing may involve effecting a chemical and/or physical reaction that changes the color in a vicinity of the sites of positive assay results or otherwise selectively deposits a colored material in a vicinity of the sites of positive assay results. In particular embodiments, sub-block 22 may comprise changing the color in a vicinity of the positive bioassay results using one or more enzymatic reaction-induced color changes. Changing the color of a substance in the vicinity of the sites of positive assay results may result in absorption of some of the laser light of optical drive 52. In still other embodiments, other chemical or physical processes may be used to alter the optical properties of the laser of optical drive 52 at or near the sites of the positive assay results. By way of non-limiting example, such processes could cause light to be absorbed, reflected, diffracted and/or scattered from the region of the of the positive assay results or may alter the wavelength, energy or polarization of light impinging on the region of the of the positive assay results.

FIG. 1A is a schematic block diagram of a method 51 for increasing the size of the site of a positive assay result which may be used to implement the sub-block 22 signal-enhancement processing in accordance with particular embodiments. Method 51 represents a particular non-limiting example of an autometallography process. Method 51 commences in block 53 which involves labeling the target biomolecules. The block 53 process of labeling the target biomolecules may be done by bonding a "labeling substance" to the target biomolecules. The block 53 labeling substance may be capable of bonding to the target biomolecules and to a "bonding substance" (discussed further below). In some embodiments, the block 53 labeling substance is capable of selectively bonding to the target biomolecules in preference to the probe biomolecules and may be applied to disc 33 after the target biomolecules have bonded to probe molecules in the sub-block 20 bioassay. In some embodiments, the block 53 labeling substance may be bonded to the target biomolecules before the target biomolecules are used in the sub-block 20 bioassay (i.e. before the target biomolecules are bonded to the probe biomolecules). In such embodiments, the labeling substance may be added to a solution containing the target biomolecules during isolation thereof, for example. In some embodiments, the block 53 labeling substance may be bonded to the target biomolecules after the sub-block 20 bioassay is completed by forming a solution containing the labeling substance and using techniques similar to those used to introduce the target biomolecules (e.g. fluidic channel plates) to introduce the labeling substance. In the FIG. 2A illustration (as shown at 120B), the block 53 labeling substance comprises biotin which forms a bond with the target DNA either before or after the target DNA bonds to the probe DNA immobilized on disc 33.

Processing method 51 then proceeds to block 55 which involves introducing a bonding substance which bonds to the block 53 labeling substance and which provides a "seed" for the size-increasing process of block 57 (discussed further below). In the illustrated embodiment of FIG. 2A, where the target biomolecules are labeled with biotin (shown at 120B), the block 55 bonding substance may comprise a conjugate of streptavidin and a gold (or other stable metal) nanoparticle (shown at 122A). The streptavidin conjugate bonds to the biotin on the target biomolecule and the gold nanoparticle provides a seed for subsequent size-increasing processing in block 57. In other embodiments, the block 55 bonding substance may comprise different materials. For example, where the block 53 labeling substance is biotin, the block 55 bonding substance may comprise a conjugate of gold (or other stable metal) and a different anti-biotin antibody (either synthetic or naturally occurring) and where the block 53 labeling substance is something other than biotin, the block 55 bonding substance may comprise a conjugate of gold (or other stable metal) with other suitable materials. In some embodiments, the seed of the block 55 bonding substance may bond directly to the block 53 labeling substance. For example, in some embodiments, the block 53 labeling substance comprises a thiol (—SH) group, in which case the gold nanoparticle seed may bond directly to the thiol (—SH) group (before or after the thiol label is bonded to the target biomolecules). In such embodiments, the block 53 labeling substance and the block 55 bonding substance may comprise a single component that may be applied in a single step and may be bonded to the target biomolecules before or after the target biomolecules are bonded to the probes. Suitable stable metals other than gold that may be used for the seed of the bonding substance include silver and/or platinum. The bonding substance may be introduced to the PC surface in a manner similar to that of the target biomolecules—e.g. by forming a solution containing the bonding substance and using fluidic channel plates to introduce the bonding substance to the PC surface.

Processing method 51 then proceeds to block 57 which involves introducing a size-increasing substance which bonds to the block 55 seed to increase the size of the positive bioassay result. In some embodiments, the block 57 size-increasing substance comprises metal (e.g. silver) nanoparticles which bond to the gold (or other stable metal) seed of the block 55 bonding substance. Such metal nanoparticles may be dissolved in solution with an optional reducing agent and introduced to the surface of optical disc 33 using a suitable channel plate (e.g. channel plate 45). As shown at 122B in FIG. 2A, the result of the block 57 size-increasing process is that the size of the site of the positive assay result is increased significantly.

The method 51 processing increases the size of the positive assay result sites on disc 33 from dimensions on the order of a few nanometers to dimensions on the order of several hundreds of nanometers. As explained in more detail below, this increase in size of the positive assay result sites causes the positive assay result sites to scatter the laser or electromagnetic beam of optical disc drive 52 and thereby result in significant errors in the data recorded on disc 33. The inventors have experimentally determined that objects having a size of about 200 nm or greater (or on the order of $\geq \lambda/4$ of the laser wavelength $\lambda$ of optical disc drive 52) result in reliably "readable" error signals.

FIG. 1B is a schematic block diagram of a method 61 for changing the color of a substance in a vicinity of the site of a positive assay result which may be used to implement the sub-block 22 signal-enhancement processing in accordance with particular embodiments. Method 61 represents one particular embodiment of a enzymatic reaction-induced color change process. Method 61 commences in block 63 which involves labeling the target biomolecules. The block 63 process of labeling target biomolecules may be similar to the block 53 labeling process (FIG. 1A) described above. The block 63 labeling substance may have characteristics similar to the block 53 labeling substance. Application of the block 63 labeling substance to the target biomolecules may be performed using techniques similar to those described above for the block 53 labeling process. In one particular non-limiting embodiment, the block 63 labeling substance comprises biotin.

Processing method 61 then proceeds to block 65 which involves introducing a bonding substance which bonds to the block 63 labeling substance and which provides an enzyme for catalyzing a color-changing reaction in block 67 (discussed further below). The block 65 process of introducing a bonding substance may be similar to the block 55 bonding substance introduction process (FIG. 1A) described above, except that the block 63 labeling substance comprises an enzyme rather than the seed used in the block 53 labeling substance. The block 65 bonding substance may comprise a conjugate of a material capable of bonding to the block 63 labeling substance and an enzyme for facilitating the block 67 color change reaction. In particular non-limiting embodiments where the target biomolecules are labeled with biotin (in block 63), the block 65 bonding substance may comprise a conjugate of an anti-biotin antibody and a suitable enzyme. In some embodiments, the anti-biotin antibody comprises streptavidin, but the anti-biotin antibody may additionally or alternatively comprise one or more other proteins (e.g. proteins which may be smaller than streptavidin). In embodiments where the block 63 labeling substance is something other than biotin, then the block 65 bonding substance may be suitably modified to provide a conjugate of an enzyme with other suitable material(s) capable of bonding to the block 63 labeling substance. As discussed in more detail below, the particular enzyme which forms part of the block 65 bonding substance depends on the particular color change reaction used in block 67. In one particular embodiment, the enzyme that forms part of the block 65 bonding substance comprises horseradish peroxidase (HRP).

After application of the bonding substance, method 61 proceeds to block 67 which involves effecting a color change reaction that takes place in the presence of the enzyme that forms part of the block 65 bonding substance. A non-limiting example of a color changing reaction is the oxidation of tetramethylbenzidine (TMB) in the presence of hydrogen peroxide ($H_2O_2$) under the influence of horseradish peroxidase (HRP):

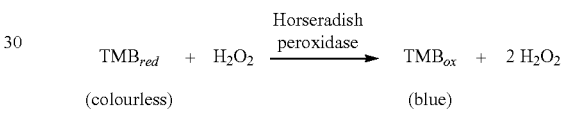

$$TMB_{red} + H_2O_2 \xrightarrow{\text{Horseradish peroxidase}} TMB_{ox} + 2 H_2O_2$$
(colourless) (blue)

In particular embodiments, a solution of $TMB_{red}$ and hydrogen peroxide may be provided on the surface of optical disc 33 and, in locations where HRP is present (e.g. in the sites of positive assay results where HRP forms part of the block 65 bonding substance), the $TMB_{red}$ is oxidized to form $TMB_{ox}$ which has a blue color and which may precipitate from the solution. Where there is no HRP present (e.g. at locations on disc 33 away from the sites of positive bioassay results), the TMB oxidation reaction does not occur at significant levels and the $TMB_{red}$ remains substantially colorless. The blue color of the $TMB_{ox}$ in the vicinity of locations of the positive bioassay results tends to absorb light from the read laser of optical disc drive 52 and thereby produce errors in the data recorded on optical disc 33. The inventors have experimentally determined that transmissivity changes greater than about 30% are sufficient to reliably cause read errors in the operation of optical disc drive 52.

It will be appreciated that the example of the oxidation of TMB in the presence of hydrogen peroxide represents one particular example of a color-change reaction. In other embodiments, other color-change reactions may be used in block 67 to provide a similar color-changing effect. It will be appreciated by those skilled in the art that the particular enzyme(s) that form part of the block 65 bonding substance will depend on the nature of the block 67 color-changing reaction. In still other embodiments, it is not particularly necessary that a color-change reaction takes place to influence an amount of laser light from optical disc drive 52 absorbed in a vicinity of the positive assay results. In some embodiments, it may be possible to influence an amount of laser light from optical disc drive 52 that is absorbed in a vicinity of the positive assay results by selectively introducing or depositing an already colored material in vicinity of the positive assay results. Such a colored material may include colored crystal particles, for example.

Returning to method 10 of FIG. 1, at the conclusion of sub-block 22, method 10 proceeds to block 16 which involves assessing the results of the block 14 bioassays using optical drive 52 to read disc 33. In the illustrated embodiment, once disc 33 containing the block 14 bioassays is mounted in optical drive 52, the remainder of block 16 may be performed by computer 50 which communicates with, and controls the operation of, optical drive 52. As shown in FIG. 1 in the course of performing the block 16 assessment, computer 50 may be configured to execute decoding software 54 and error mapping software 56 which are described in more detail below.

In general, the block 16 assessment of the results of the block 14 bioassay involves detecting errors in the digital data recorded on optical disc 33 (using the error-detection redundancies associated with the digital data) and correlating these errors with positive bioassay results (e.g. by correlating these errors with particular test sites 43 on disc 33 exhibiting positive bioassay results). The block 16 assessment process starts with error detection in sub-block 24. The sub-block 24 error detection is based on the error-detection redundancies in the data recorded on optical disc 33 (see above description of block 12) and may be performed by computer 50 executing data decoding software 54. The error detection process of sub-block 24 may involve reading digital data recorded on optical disc 33 (including both data payload and error-correction redundant data) using conventional optical disc drive 52 and decoding the digital data to ascertain the presence of errors. Decoding the data in sub-block 24 may involve a process that is the inverse (i.e. conjugate) of the encoding process used to impart the error-detection redundancies into the payload data for recording on optical disc 33. In particular embodiments, the block 24 decoding process may involve extracting the error-detection redundancies from the payload data and verifying the accuracy of the recorded data. The sub-block 24 error-detection process may involve a thresholding process involving error density and/or a number of errors, wherein an error density and/or a number of errors over a certain threshold is determined to be positive assay result. The threshold may be a factor of 3 or more (in some embodiments 10 or more) greater than an error density and/or number of errors which may be expected on a normal optical disc not subjected to the sub-block 20 bioassay or the block 22 processing. The threshold may be a factor of 3 or more (in some embodiments 10 or more) greater than a an error density and/or number of errors at locations spaced apart from the positive bioassay results.

As discussed above, in particular embodiments (eg. where CD audio data is recorded on disc 33 and/or DVD video data is recorded onto optical disc 33), the data recorded on optical disc 33 is encoded using a Reed-Solomon CIRC error detection technique. These Reed-Solomon CIRC techniques use a data interleaving process to encode and distribute payload data and employ redundant parity bits to protect the accuracy of the payload data. In such embodiments, the sub-block 24 error detection process may involve extracting the parity bits from the data payload and verifying the accuracy of the recorded data. Any disagreement during the parity check (e.g. a disagreement between the expected parity bits (as determined from the payload data read in optical drive 52) and the parity bits read directly from disc 33 in optical drive 52) is indicative of an error. More specifically, in such embodiments, the CD audio data or DVD video data (including payload data and redundant data) read from optical disc 52 may be decoded and each frame (including payload data and redundant data) may be processed by computer 50 executing decoding software 54 to detect the presence of errors. Accordingly, in such embodiments, errors in the payload data may be detected on a frame-by-frame basis. In the case of audio data, each frame contains 24 bytes of audio payload data and 8 bytes of parity data. The use of encoding schemes that make use of frames is not limited to CD audio data and DVD video data. In any embodiments where the encoding scheme used to record digital data and its error-checking redundancies onto disc 33 makes use of frames, the block 24 process of identifying errors may be performed on a frame-by-frame basis.

After processing in sub-block 22, the sites of positive assay results on optical disc 33 will comprise relatively large conglomerations on the PC surface of optical disc 33 (in the case where the sub-block 22 processing involves increasing the size of the site of positive assay results) and will therefore scatter the laser of optical disc drive 52 resulting in the block 24 detection of errors in the recorded data. Similarly, in the case where the sub-block 22 processing involves color changes in a vicinity of the sites of positive assay results, the laser of optical disc drive 52 may be absorbed resulting in the block 24 detection of errors in the recorded data. For the case of sub-block 22 size-increasing processing, FIG. 2E schematically depicts laser 82 of optical drive 52 being directed through lens 83 of optical drive 52 and scattering upon interaction with CD-R optical disc 33 prepared in accordance with blocks 12 and 14 described above. CD-R optical disc 33 comprises a dye layer 74 onto which data 72 has been recorded. In the illustrated embodiment, optical disc 33 has a positive assay result formed on its PC surface 76. In the illustrated embodiment, this positive assay result comprises a plurality of biomolecules 78 having metal nanoparticle(s) 80 (e.g. gold and silver) bonded to the target biomolecules 78. As discussed above, the conglomerate of biomolecules 78 and nanoparticle(s) 80 may have dimensions on the order of several hundred nanometers. The size of these conglomerates is sufficient to scatter the read laser 82 of optical drive 52 as shown at 84 and to generate corresponding errors when computer 50 attempts to evaluate recorded data 74 using data decoding software 54 in sub-block 24.

After detection of errors in sub-block 24, the block 16 assessment process proceeds to sub-block 26 which involves mapping the detected error(s) to specific location(s) on the surface of optical disc 33. Sub-block 26 may be performed by computer 50 executing error mapping software 56. Error mapping software 56 is capable of mapping errors in the recorded data to corresponding physical locations on the surface of optical disc 33. In particular embodiments, where the recorded data on optical disc 33 comprises audio CD data, DVD video data or other data encoded with error-checking redundancy on a frame-by-frame basis, data decoding (error detection) software 54 is capable of identifying particular data frames containing errors and, as a part of sub-block 26, error mapping software 56 maps the data frames containing errors to specific physical locations on optical disc 33. As discussed above, the data recorded on optical disc 33 is not limited to audio CD data or DVD video data but may generally comprise other data encoded with error-detection redundancies. In such embodiments, error mapping software 56 is provided with some information or scheme about the digital data recorded on disc 33 and computer 50 running error mapping software 56 uses this information or scheme in block 26 to identify the location(s) on disc 33 where errors have occurred.

The block 16 assessment process then proceeds to sub-block 28 which involves determining positive bioassay results. Since the on-disc locations of errors determined in sub-block 26 correspond to the on-disc sites of positive assay results, the result of the sub-block 24 error mapping process may be used in sub-block 26 to determine the locations of positive bioassay results. As discussed above, the block 20 preparation of the bioassay involves knowing or estimating locations of test sites 43 (FIG. 2D). The locations of test sites 43 may be based on knowledge of the locations of channel plates 39, 45, for example. Sub-block 28 may involve a thresholding process involving error density and/or a number of errors, wherein an error density and/or a number of errors over a certain threshold is determined to be positive assay results. The threshold may be a factor of 3 or more (in some embodiments 10 or more) greater than an error density and/or number of errors which may be expected on a normal optical disc not subjected to the sub-block 20 bioassay or the block 22 processing. The threshold may be a factor of 3 or more (in some embodiments 10 or more) greater than an error density and/or number of errors at locations spaced apart from the positive bioassay results. Sub-block 28 may involve correlating the on-disc locations of detected errors and the on-disc locations of test sites 43. Assuming the particular probe and target biomolecules are known for each of test sites 43, the correlation between the on-disc locations of detected errors and the on-disc locations of test sites 43 may be used in sub-block 28 to determine particular pairs of probe and target biomolecules that generate positive bioassay results.

it will be appreciated by those skilled in the art, that the functions of data decoding software 54 and error mapping software 56 may be combined. Several optical disc quality diagnostic programs which may be used to accomplish some or all of the functions of data decoding software 54 and error mapping software 56 are available for public download. Such disc quality diagnostic programs include, for example: Plex-Tools® Professional available from (http://www.plextools.com/); kprobe (available from http://www.k-probe.com/); and Nero™ CD-DVD Speed (available from http://www.cdspeed2000.com/). These software tools are particular to optical discs 33 onto which CD audio data or DVD video data has been recorded. When running on a computer 50, these software tools process error statistics corresponding to data read from optical disc 33 by optical drive 52 and generate data (e.g. plots) displaying the variation of block error rate as a function of playtime (i.e. the time that the CD audio/DVD video data has been playing back). Because the playtime corresponds to a specific physical location on the surface of optical disc 33, positive assay results can be assessed provided that the positive assay results cause significant disruptions to the laser reading of optical drive 52.

Figure 3A:
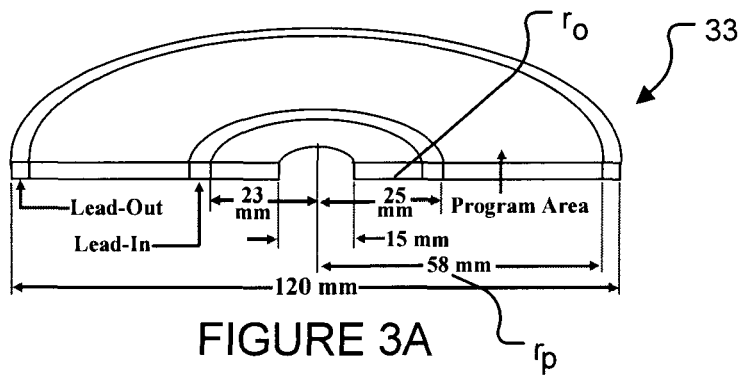
FIG. 3A is a schematic depiction of various parameters of a standard optical CD-R disc.

If an error can be identified at a particular playtime (t), then the radial location (r) of the error on the surface of disc 33 may be identified according to the following equation:

$$\frac{t}{\tau} = \frac{r^2 - r_o^2}{r_p^2 - r_0^2} \quad (1)$$

where:
t is the playtime of the detected error;
r is the radial location of the detected error on the disc surface;
$r_o$ is the radius of the non-programmable central region of the disc;
$r_p$ is the radius of the programmable region of the disc; and
τ is the total recordable time of the disc.
A non-limiting example showing the components of equation (1) is schematically depicted in FIG. 3A for a typical 700-MB CD-R disc 33 which has a non-programmable central region of $r_o$=25 mm, a programmable region of $r_p$=58 mm and is capable of recording τ=79.7 min of CD audio data. If an error peak occurs at around t=15 min in the error distribution plot, equation (1) can be used to determine that the biomolecular binding event (positive assay result) happened at an approximate radial location having a radius r=33.77 mm.

It will be appreciated by those skilled in the art that the parameters and/or form of equation (1) may be modified for different optical discs 33 and/or for different data recorded onto such optical discs 33. Furthermore, it is not necessary that the data recorded onto optical disc 33 have a "playback time". In more generalized embodiments, it is merely necessary that computer 50 operating data decoding software 54 and error mapping software 56 be able to map the location of an error back to a physical location on disc 33 so as to identify the on-disc locations of the sites of positive assay results.

In particular embodiments, the bioassays assessed using method 10 may comprise so-called "sandwich" bioassays where a labeling substance can be introduced to the PC surface of disc 33 after the target biomolecules have bonded to the probe biomolecules. The labeling substance may be applied as a part of block 53 or block 63 described above. In one particular embodiment, method 10 may be used to assess a sandwich bioassay involving Protein A, which is a membrane protein located on the surface of a pathogenic bacteria *Staphylococcus aureus*, which may be found, for example, in a person's nose or skin and which may cause a wide range of illnesses ranging from minor infections to life-threatening diseases. *Staphylococcus aureus* often bonds to a wide range of IgGs, thereby escaping phagocytosis by the host's immune system. A sandwich structure may be constructed by: causing a probe anti-Protein A antibody to be bonded to the activated PC surface of optical disc 33; introducing a Protein A target to the PC surface of optical disc 33 so that the target Protein A bonds to the probe anti-Protein A; and introducing a second anti-Protein A antibody labeling substance to the surface of disc 33 to bond to the target Protein A. The second anti-Protein A antibody labeling substance may be different than the probe anti-Protein A antibody, so that the second anti-Protein A antibody labeling substance and the probe bond to the Protein A target at different bonding sites.

The resulting sandwich bioassay may then be processed in accordance with the remainder of method 51 or 61 (as the case may be) and assessed in accordance with block 16 as described above. In some embodiments, a gold nanoparticle seed may be directly bonded to the second anti-Protein A antibody (before or after introduction of the second anti-Protein A antibody to the surface of disc 33). In such embodiments, the second anti-Protein A antibody may function in a manner similar to both the block 53 labeling substance and the block 55 bonding substance described above. Similarly, in some embodiments, an enzyme may be directly bonded to the second anti-Protein A antibody (before or after introduction of the second anti-Protein A antibody to the surface of disc 33). In such embodiments, the second anti-Protein A antibody may function in a manner similar to both the block 63 labeling substance and the block 65 bonding substance described above.

In general, the use of a second antibody as a part of, or as, a labeling substance in a sandwich bioassay is not limited to bioassays involving Protein A targets. It will be appreciated that similar second antibodies could be used as a part of, or as, a labeling substance for bioassays involving other biomolecule targets.

In another exemplary embodiment, method 10 may be used to assess a sandwich bioassay involving thrombin, which is a serine protease that plays an important role in the blood clotting cascade. A sandwich structure may be constructed by: causing a probe anti-thrombin antibody to be bonded to the activated PC surface of optical disc 33; introducing a target (thrombin) to the PC surface of optical disc 33 so that the target thrombin bonds to the probe anti-thrombin antibody; and introducing an aptamer labeling substance to the surface of disc 33 to bond to the target thrombin. An aptamer is a synthetic molecule comprising a specified nucleic acid sequence. An aptamer sequence suitable for binding to thrombin is shown below in bold:

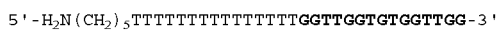

The aptamer labeling substance may bond to the thrombin at a different bonding site than the probe anti-thrombin antibody. The resulting bioassay may then be processed in accordance with the remainder of method 51 or 61 (as the case may be) and assessed in accordance with block 16 as described above. In some embodiments, the aptamer labeling substance may be labeled with biotin in a manner similar to that described above (block 53 or block 63). In such embodiments, the aptamer may be labeled with biotin prior to application to disc 33 and then the aptamer/biotin labeling substance may be introduced to disc 33 after the target biomolecule has bonded to the probe biomolecules. In such embodiments, introduction of a bonding substance (block 55 or block 65) and increasing the size of the positive assay result (block 57) or effecting a color change reaction (block 67) may be substantially similar to the processes described above.

In general, the use of an aptamer as a portion of, or as, a labeling substance in a sandwich bioassay is not limited to bioassays involving Thrombin targets. It will be appreciated that similar aptamers could be used for as a part of, or as, a labeling substance for bioassays involving other biomolecule targets.

The inventors conducted a number of experiments intended to evaluate the methods and systems described above. Using ink to stain optical discs 33, the inventors determined that spot sizes on the order of ~260 µm were able to generate consistently detectable increases in error density for optical discs 33 onto which CD audio data was recorded. It is expected that the detectable resolution may be made smaller, but that there may be a limitation to detectable error resolution based on the size of the laser spot of optical drive 52. It is expected, for example, that a DVD optical drive 52 with a relatively small laser spot will be capable of detecting errors with a higher resolution (i.e. smaller spot size) in comparison to a CD optical drive 52 with a relatively large laser spot.

Experiment #1

Biotin-Streptavidin Bioassays

Five binding strips containing biotin were immobilized on the PC surface of an optical disc recorded with CD audio data and activated with a combination of UV and ozone. The biotin binding strips were immobilized with the assistance of PDMS fluidic plates. The surface bound biotin was prepared by coupling biotinyl-3,6,9-trioxaundecanediamine to the carboxylic acid groups on the activated PC surface of the optical disc. The biotin binding strips were then reacted with five different concentrations (0.1, 0.2, 0.4, 0.8 and 1.6 µg/ml) of gold nanoparticle-streptavidin conjugate provided in 1.0 µl microfluidic channels.

Figure 4A:
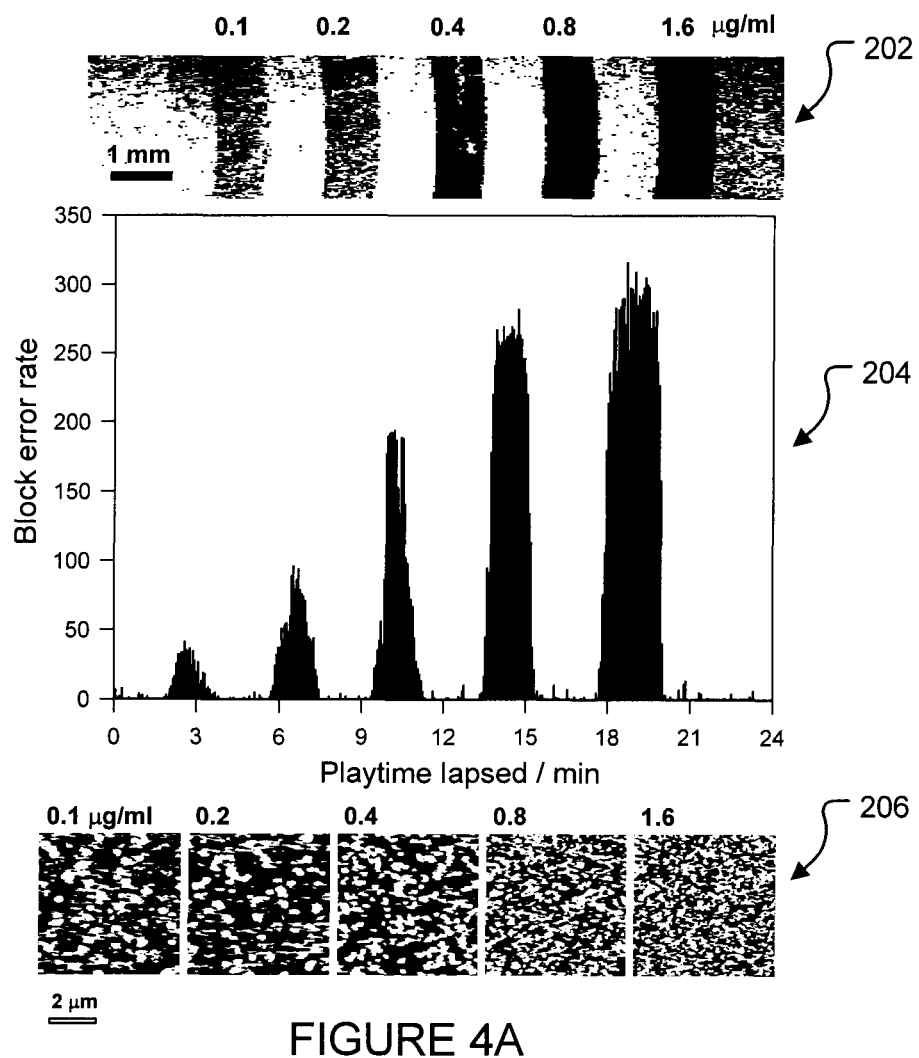
FIG. 4A shows an optical image, a block error rate distribution and a atomic force microscopy (AFM) image of a series of the biotin-streptavidin binding sites of experiment #1.

The surface of the disc was then subjected to the silver enhancement reaction (see step 22B of FIG. 2A) for 50 minutes which caused the binding sites to become dark (see the optical image 202 of the CD surface in FIG. 4A). Atomic force microscopy (AFM) images 206 (FIG. 4A) revealed that the biotin-streptavidin binding sites comprised relatively large-sized nanoparticles (having dimensions on the order 90-300 nm). AFM images 206 also revealed that the size of the nanoparticles gradually decreased but the particle densities of the nanoparticles gradually increased with increasing streptavidin concentration. Without wishing to be bound by any particular theory, it is currently thought that the particle size and density variations may be due to differences in the number of gold-nanoparticle "seeds" and the effects of competitive growth.

Figure 4B:
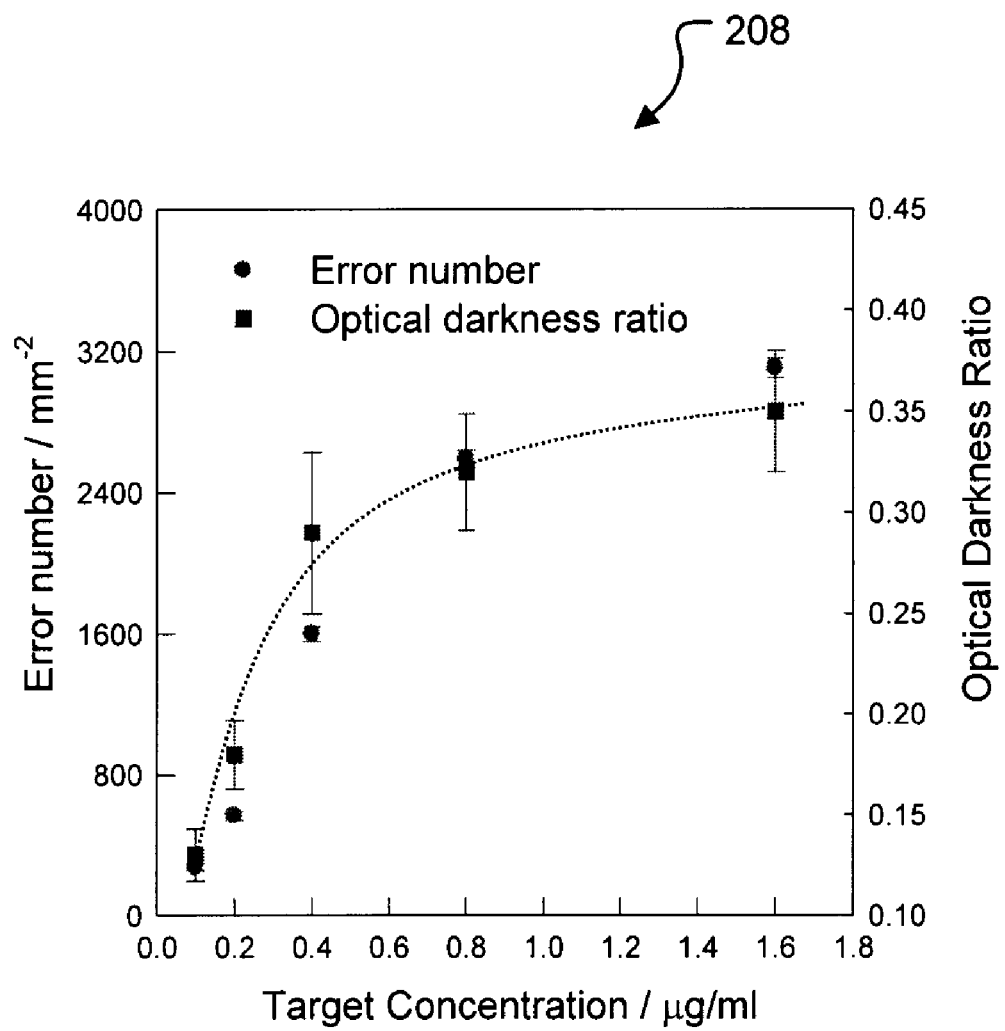
FIG. 4B is a plot showing the relative error density and optical darkness ratio for the five different target concentrations used in experiment #1.

When the optical disc was read in an optical disc drive, the CD audio data recorded on the optical disc exhibited a characteristic error distribution 204 with five peaks (FIG. 4A) whose positions (playtime) matched well with the corresponding physical positions of the binding strips on the disc. The ordinate axis of the FIG. 4A plot is referred to as the block error rate. As used herein, the block error rate is an error density measurement which refers to the number of errors in a block (also known as a sector) of recorded data. For CD audio data, one block of recorded data contains 98 frames and each frame of recorded data comprises 33 bytes (24 bytes of audio data, 8 error correction bytes and one subcode byte). In the case where the data recorded on the disc can be played back, a block of recorded data may be converted to units of playback time, hence the reason for the term block error "rate". The block error rate may be term particular to discs onto which audio CD data is recorded. For other types of optical discs and/or other types of recorded data, the block error rate may be considered to be an error density measurement. The data 208 plotted in FIG. 4B demonstrate that both the error density (in number of errors per mm$^2$ and the optical darkness ratios (ODR) of the binding sites (determined with an optical microscope) depend on the concentrations of the target biomolecules. The optical darkness ratio (ODR) is defined by equation (2):

$$\text{ODR} = (I_b - I_s)/I_b \qquad (2)$$

where $I_b$, is the average luminosity of the background and $I_s$ the luminosity of the binding site which is a function of particle size and density. The FIG. 4B plot shows that for low target concentrations, error density and ODR are approximately proportional to the concentration of the target molecules (streptavidin) and for higher target concentrations, both the error density and the ODR reach a plateau.

Experiment #2

Matched DNA Bioassays

The DNA probes and biotinylated DNA targets used for the DNA bioassay experiments are shown in Table 1.

TABLE 1

| Oligonucleotide sequences of probe and target DNA samples | |
|---|---|
| DNA strand reference | Sequence |
| Probe I | 5'-amino-C6-CGC CGA TTG GAC AAA ACT TAA A-3' |

TABLE 1-continued

Oligonucleotide sequences of
probe and target DNA samples

| DNA strand reference | Sequence |
|---|---|
| Probe II | 5'-amino-C6-CGC CGA TTG GAG AAA ACT TAA A-3' |
| Probe III | 5'-amino-C6-TTT AAG TTT TGT CCA ACT GGC G-3' |
| Target I | 3'-GCG GCT AAC CTG TTT TGA ATT T-5'-biotin |
| Target II | 3'-GCG GCT AAC CTG TTT TGA ATT T-5'-Cy5 |

A line array was prepared on the activated PC surface of an optical disc by immobilizing DNA Probe I on the PC surface and hybridizing Probe I with increasing concentrations (25 nM, 0.1 µM, 0.25 µM, 1.0 µM and 4.0 µM) of biotinylated DNA Target I using 1.0 µl microfluidic channels in accordance with the techniques described above. The assays were subsequently treated with a gold-streptavidin conjugate solution and enhanced with silver nanoparticles according to the processing procedures of sub-block 22 (procedures 22A, 22B) described above. The results of this experiment are shown in the optical image 212 and block error rate distribution 214 of FIG. 5A and in the error density and ODR data 218 plotted in FIG. 5B.

Optical image 212 and block error rate distribution 214 show that after the block 22 metalization processing, the DNA hybridization array became optically visible and also readable by an optical drive. The data 218 plotted in FIG. 5B show that the error density and ODR values increase rapidly with target concentration in the low concentration range and reach saturation levels at higher concentrations of complementary DNA target strands.

Figure 5A:
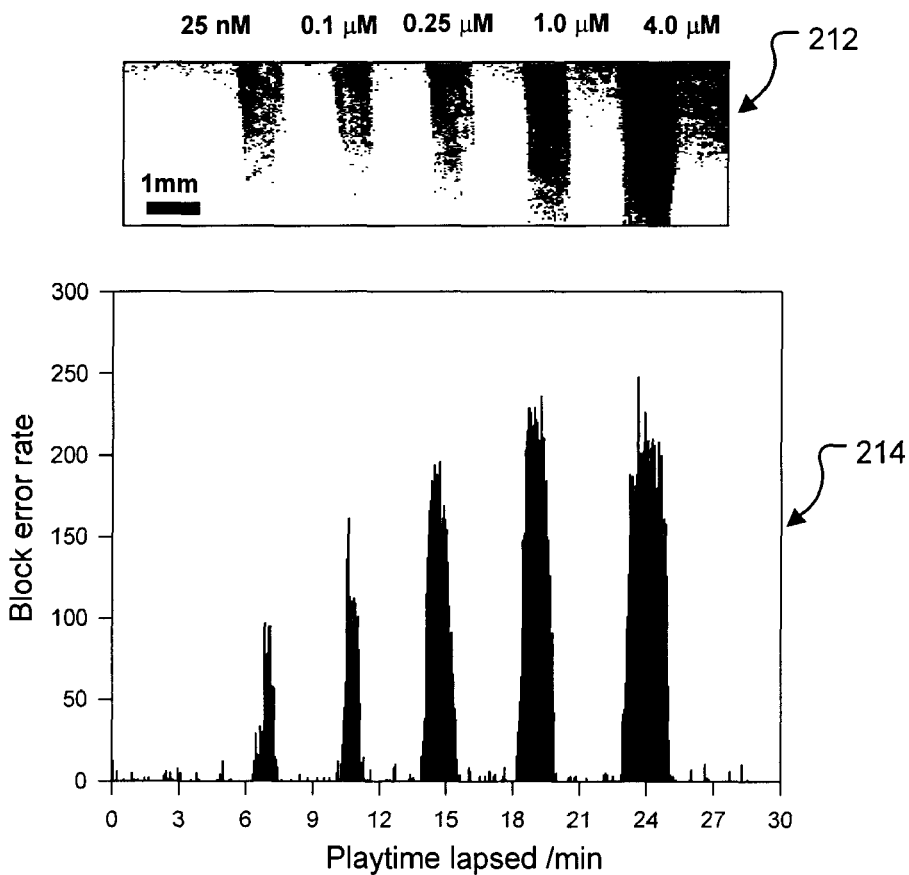
FIG. 5A shows an optical image and a block error rate distribution of the DNA binding sites of experiment #2.
Figure 5B:
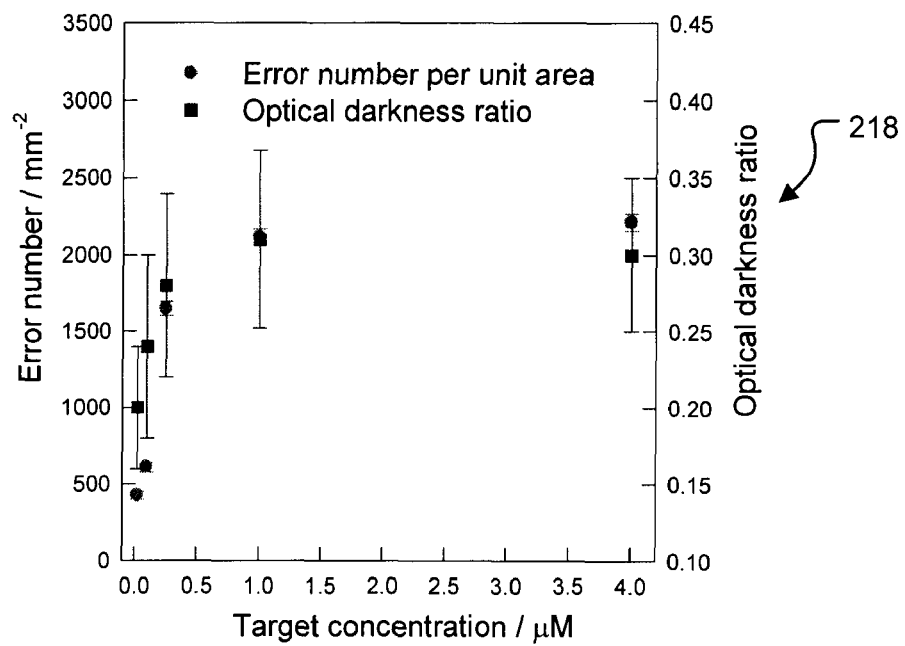
FIG. 5B is a plot showing) the relative error density and optical darkness ratio for the five different target concentrations used in experiment #2.

The data shown in FIGS. 5A and 5B show that the hybridization of the DNA biomolecules are detectable at target concentrations as low as 25 nM. The results shown for the FIGS. 5A and 5B target concentration of 25 nM resulted from the use of only 1.0 µl of target solution (i.e. 25 fmol of DNA molecules). Accordingly, the sensitivity achieved in experiment #2 is an order of magnitude better than that of prior art fluorescence labeling/scanning methods.

Experiment #3

Mismatched DNA Bioassays

Figure 6:
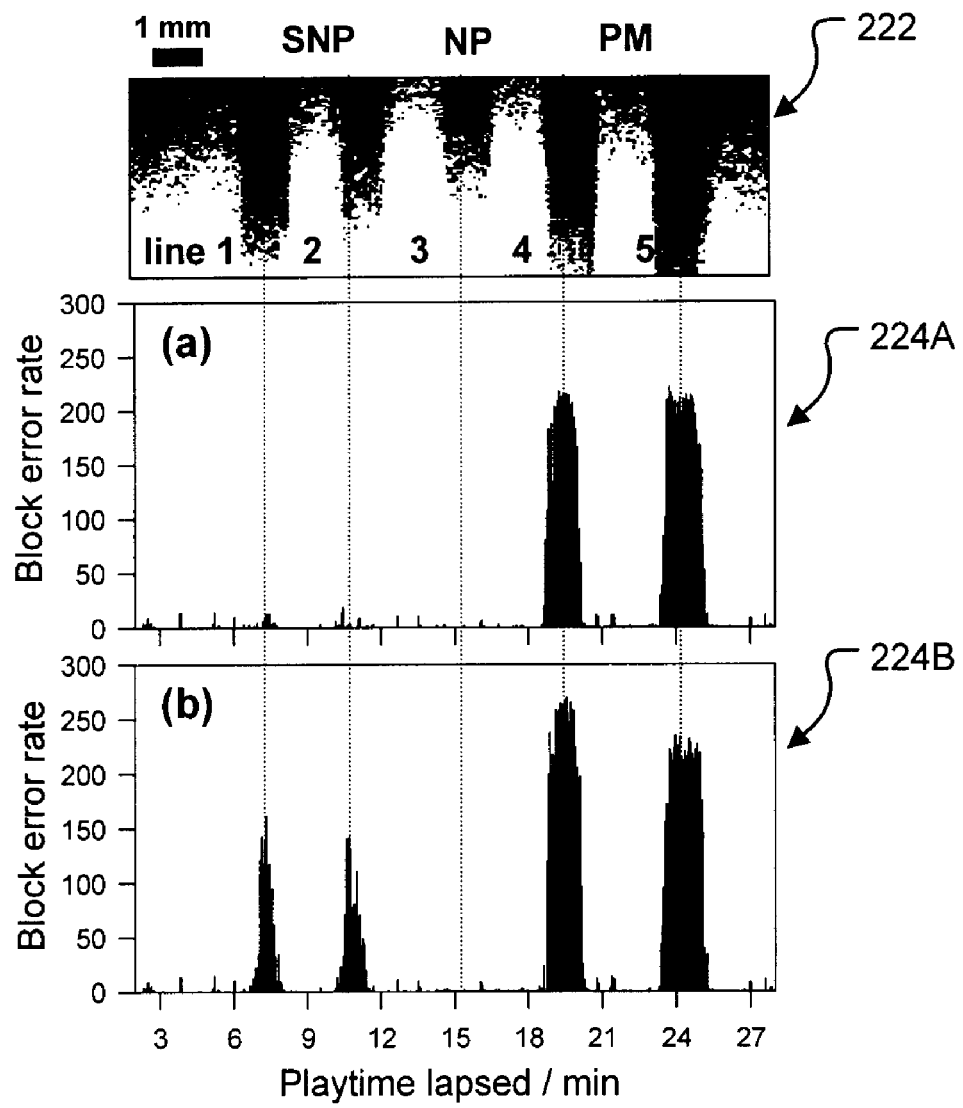
FIG. 6 shows an optical image and a pair of block error rate distributions of the DNA binding sites of experiment #3 after silver treatment for different periods of time.

In this experiment, three different DNA probes (Probe I, Probe II and Probe III) were immobilized on the activated PC substrate of an optical disc according to the process described above and were then hybridized with the same DNA target (Target I). It will be appreciated that Target I and Probe I are complimentary, Target I and Probe II have a single-base-pair mismatch (i.e. a single-nucleotide polymorphism (SNP)) and Target I and Probe III represent non-complementary probe strands. FIG. 6 shows an optical image 222 and block error rate distributions 224A, 224B for the matched pair of Target I and Probe I (vertical lines 4 and 5 of FIG. 6), the SNP of Target I and Probe II (vertical lines 1 and 2 of FIG. 6) and for the mis-matched pair of Target I and Probe III (vertical line 3 of FIG. 6).

Plot 224A shows the block error rate distribution for 60 minutes of silver nanoparticle treatment (step 22B of FIG. 2A) and plot 224B sows the block error rate distribution for 80 minutes of silver nanoparticle treatment. Plots 224A, 224B show that: (i) the hybridization of complementary DNA strands (vertical lines 4 and 5) is detectable after silver treatment for a relatively short period of time; (ii) after a sufficiently long period of silver treatment time, weaker error peaks resulting from hybridization of the SNP DNA pairs (vertical lines 1 and 2) are also detectable; and (iii) no hybridization is detectable from the non-complementary probe strands (vertical line 3).

Experiment #4

Anti-Human IgG/Human IgG Assays

The inventors also conducted an experiment for detecting binding of various concentrations (25 ng/ml 50 ng/ml, 0.1 µg/ml, 0.25 µg/ml and 1.0 µg/ml) of anti-human IgG to human IgG immobilized on the activated PC surface of an optical disc in accordance with the process described above. The immobilization of proteins on the surface of an optical disc may be relatively challenging (when compared to DNA, for example) because proteins can lose activity relatively easily. The results of this experiment are shown in the optical image 232 and block error rate plot 234 of FIG. 7A and in the error density and ODR data 238 of FIG. 7B.

Figure 7A:
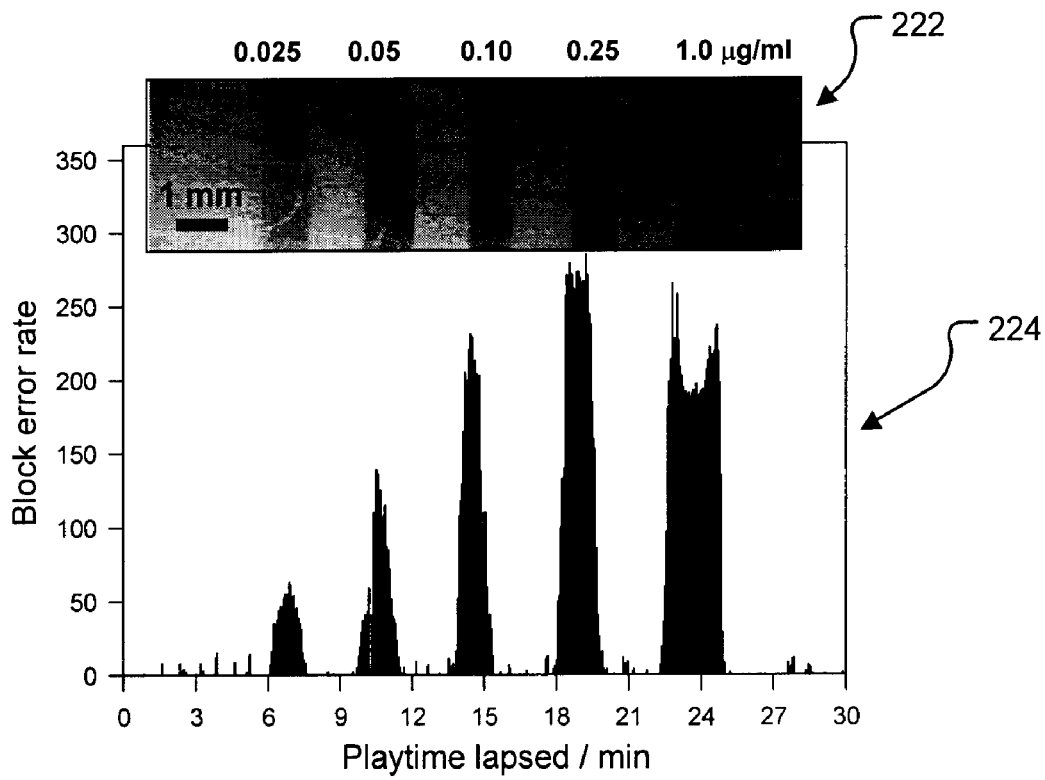
FIG. 7A shows an optical image and a block error rate distribution of the anti-human IgG/human IgG binding sites of experiment #4.
Figure 7B:
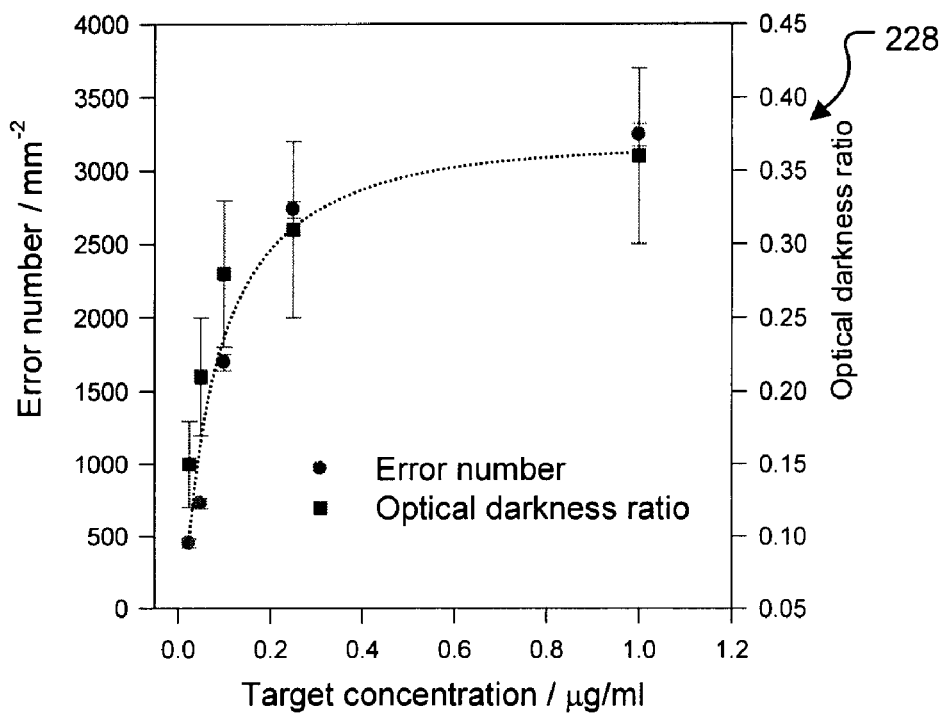
FIG. 7B is a plot showing) the relative error density and optical darkness ratio for the five different target concentrations used in experiment #4.

Block error rate plot 234 of FIG. 7A shows that the error detection sensitivity may be higher for the binding of anti-human IgG to human IgG (at some concentrations) than for similar concentrations of DNA (see block error rate plot 214 of FIG. 5A). Block error rate plot 234 also shows that a readable signal was obtained with a target (anti-human IgG) concentration as low as 25 ng/mL. The error density data 238 plotted in FIG. 7B shows that the error density saturation level for binding of anti-human IgG to human IgG is reached at a much lower target concentration (~250 ng/mL) when compared to DNA hybridization (~1 µg/mL). In addition, the duration of the silver treatment (step 22B of FIG. 2A) which resulted in the plots of FIGS. 7A and 7B was only 30 min, which confirms the high efficiency of IgG immobilization and of anti-IgG binding.

Supplemental Information Relating to Experiments

The information in this section provides further details relating to the experiments described above.

Surface Reactions on CD-R optical discs: Before reaction, CD audio information was burned onto blank CD-R (Mitsui Inc.) optical discs. After recording the CD audio information, the PC surfaces of the discs were cleaned with ethanol and then activated by irradiating the discs in the presence of ozone in a UV/ozone chamber (Model PSD-UV, Novascan Technologies, Inc.) for 15 minutes (see the Surface Activation Application). The discs were subsequently immersed in a 0.1 M phosphate buffer at pH 6.0 (also containing 5 mM 1-ethyl-3-(3'-dimethylaminopropyl)-carbodiimide (EDC) and 0.33 mM N-hydroxysuccinimide (NHS)) for 5 hours. Then, three kinds of probe biomolecules—amine-PEO3-biotin (biotinyl-3,6,9-trioxaundecanediamine, Pierce Biotechnology Inc.), amino-modified DNA strands (Sigma-Genosys, sequences listed in Table 1) and human IgG (Athens Research & Technology Inc.), respectively—were immobilized onto the activated PC surfaces of the optical discs. The immobilization of these probe biomolecules was followed by on-disc binding with their corresponding target molecules: gold-conjugated streptavidin (1.4 nm diameter, Nanoprobes Inc.), biotinylated DNA target (Sigma-Genosys) and biotinylated goat anti-human IgG (biotin-SP-conjugated Goat anti-Human IgG (H+L), Jackson ImmunoResearch Inc.).

Experiment #1

Biotin-Streptavidin Binding

After the NHS activation step, 10 µL of a 30 µM solution of amine-PEO3-biotin in 0.1M phosphate buffer at pH 7.0 were delivered onto the PC surface through a mask (made from a PDMS plate), and the disc was kept in a humid box for 5 hours. After the PDMS mask was peeled off, the reaction zone was passivated by treatment with a 20 mM phosphate blocking buffer at pH 7.4 (containing 150 mM NaCl, 0.8% bovine serum albumin (BSA), 0.1% gelatin, 0.05% Tween 20 and 0.05% $NaN_3$) for 15 minutes to reduce non-specific adsorption. Then a second PDMS plate with 6 microchannels oriented perpendicularly was placed on top of the disc. Five different concentrations of gold-conjugated streptavidin solutions (0.1, 0.2, 0.4, 0.8 and 1.6 µg/mL) in 20 mM phosphate buffer (pH 7.4, 150 mM NaCl, 0.1% BSA, and 0.05% NaN3) were injected into the channel reservoirs on one side and passed through the channels by suction from the other ends. The solutions were allowed to stay in the channels for 60 minutes at room temperature. After the PDMS plate was peeled off, the disc was washed with the 0.M phosphate buffer at pH=7.0, dried under $N_2$ and subjected to the silver treatment.

Experiments #2 and #3

DNA Hybridization

After DNA Probe immobilization, the PC surface was passivated by treatment with 1 mg/mL solution of BSA for 5 minutes. Five concentrations of DNA target solution (0.025, 0.1, 0.25, 1.0 and 4.0 µM Target I) in 1×SSC (Saline-Sodium Citrate) buffer (pH=7.0, 150 mM NaCl, 15 mM sodium citrate, 0.05% sodium dodecylsulfonate) were hybridized in a humid box at 40° C. for at least 30 minutes with three different DNA probe sequences (Probes I, II, and III, see Table 1). After hybridization, the disc was washed with SSC buffer, treated with phosphate buffer for 20 min, and immersed in 0.4 µg/mL gold-conjugated streptavidin solution for 60 min. Then the disc was washed and subjected to the silver treatment.

Experiment #4

Antigen-Antibody Interaction

Human IgG (250 µg/mL) in 20 mM PBS-BSA buffer were allowed to react with the NHS-activated PC surface for 2 hours at room temperature. The disc surface was then washed with phosphate buffer for 20 minutes, five concentrations of anti-human IgG solution (0.025, 0.05, 0.10, 0.25 and 1.0 µg/mL) were delivered, and the disc was incubated for 90 min.

Silver Treatment: For the silver treatment, the biomolecule-modified discs were thoroughly washed with distilled water to remove anions (especially chloride). After washing, they were immersed in freshly made silver enhancement solution for different periods of time. A reagent kit for silver enhancement reaction (LI Silver, Nanoprobes Inc.), which consists of two solutions, silver salt (silver acetate) and reducing agent (hydroquinone) respectively, was used as directed. More particularly, two solutions (silver acetate and hydroquinone with concentrations of 10 mM and 5 mM) were mixed immediately prior to introduction into the microfluidic channels and allowed to react with the gold seeds at room temperature.

Assessment of Bioassays in Optical Drives: The experiments described above were conducted using three different systems (optical drive and corresponding data decoding/error mapping software), including:

(i) Plextor PX-755UF CD/DVD writer and PlexTools® Professional;
(ii) Plextor PX-760A CD/DVD writer and PlexTools® Professional; and
(iii) Liteon SHW-160P6S CD/DVD writer and kprobe.

PlexTools® Professional runs on Windows™ based PCs and was used to generate the error plots shown in the Figures. For error tests, PlexTools® Professional controls the CD drive to run at an 8× speed, so that it typically takes 10 minutes to screen the entire CD and several minutes to screen a specified zone. After reading, PlexTools® Professional will export an error distribution plot and provide a statistical result on error numbers and types.

Optical/AFM Imaging and Data Analysis: Optical images of all samples were captured by a Motic Digital Microscope (DM143, Micro-Optic Industrial Group Co.), and analyzed by measurement of position and size (area) of each binding strip upon silver treatment. The optical darkness ratio (ODR) of each strip was determined by measuring its average intensity ($I_s$) using the luminosity histogram tool of Adobe™ Photoshop™, and compared to the value for the background luminosity ($I_b$). The surface topographies of the binding assays were examined with an MFP-3D-SA Atomic Force Microscope (Asylum Research, Inc.) in contact mode using a rotated monolithic silicon tip (Innovative Solutions Bulgaria Ltd., resonance frequency 13 kHz, force constant 0.2 N/m). The number, size and morphology of the particles after silver treatment were analyzed with IGOR Pro 4 software.

Supporting Information

Figures 3B, 3C:
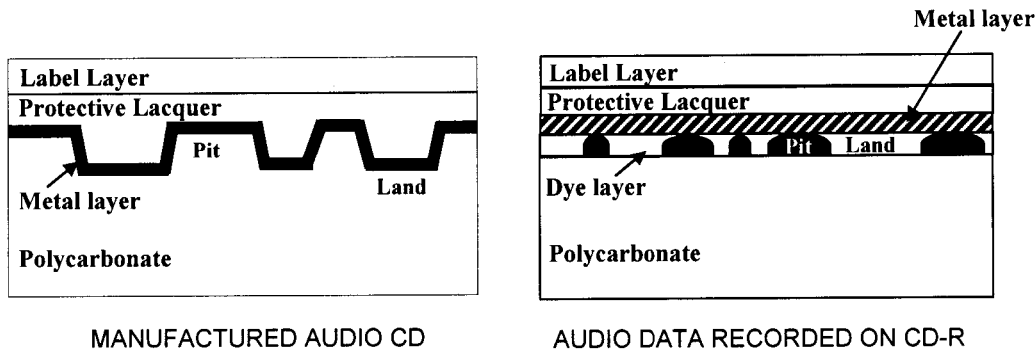
FIG. 3B is a schematic partial cross-section of a manufactured audio CD optical disc.
FIG. 3C is a schematic partial cross-section of a CD-R optical disc onto which audio data has been recorded.

Standards of Audio CDs and Audio CD-R optical discs: One type of optical disc that may be used in connection with particular embodiments of the invention is the compact disc (CD) which may have audio data recorded thereon. Audio CDs may have digital audio data imparted thereon during fabrication of the disc. Such "manufactured" audio CDs typically include a 1.2 mm thick polycarbonate (PC) substrate with molded "pit/land" features representing digital data. A schematic partial cross-section of a manufactured audio CD is shown in FIG. 3B. A lower metal reflective layer (~50 nm in thickness) is protected by a lacquer layer that supports the label layer. Audio data may also be recorded onto CD-R optical discs. A schematic partial cross-section of a CD-R onto which audio data is recorded is shown in FIG. 3C. The CD-R has an additional dye layer which can be converted locally from transparent to opaque by the laser beam of a optical disc burner. The transparent and opaque regions of the CR-R dye layer simulate the physical pits and lands in manufactured audio CDs. Stored digital data are represented by pits and lands (manufactured CD) or by opaque and transparent spots (recorded CD-R).

CDs and CD-Rs, irrespective of their format (CD Audio, CD-ROM, CD-Text etc), have the same physical specifications (known as the "red book" specifications). A standard CD is a 120-mm-diameter circular disc with a 15-mm-diameter hole at the center. The annular space between the central hole and the periphery of the disc is divided into three areas: lead-in (23-25 mm radius from the center) for index information, program area (25-58 mm) containing the digital data and lead-out (58-60 mm) with digital silence information. The size of the program area is $\pi(58^2-25^2)=27397\pi$ mm$^2$ For CDs or CD-Rs onto which audio information is recorded, audio information is stored in different tracks of the program area. The physical positions of the tracks (including start and playtime) are defined in a table of contents (TOC). Audio CDs are played with a constant linear velocity (CLV), which means the digital capacity (playtime) of each audio block is proportional to its recording area. The playing time can be calculated from the size of the program area, the linear velocity (~1.2-1.4 m/s) and the track pitch (~1.5-1.7 μm). For a 700-MB audio CD, the maximum playtime is 4780 seconds or 79.7 minutes.

Figure 3D:
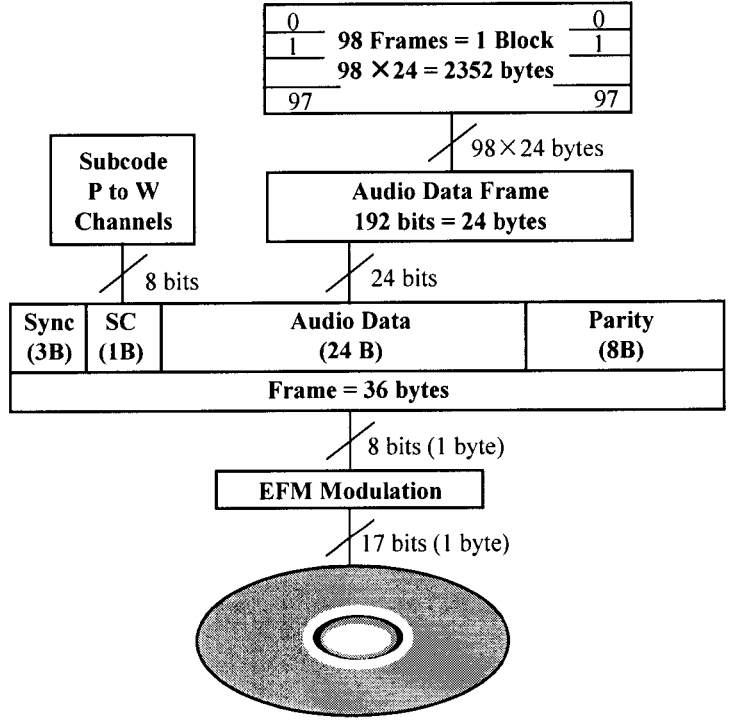
FIG. 3D is a schematic diagram showing the organization of audio data recorded onto a CD or CD-R.

FIG. 3D shows a schematic diagram illustrating the standard organization of data for a CDs or CD-Rs onto which audio information is recorded. In the audio CD standard, the base unit of audio information is the frame which contains 24 bytes of audio data, 8 bytes of parity bits, 3 bytes of sync data and 1 byte of sub-code bits. The 8 bytes of parity bits protect (i.e. provide error detection and correction capabilities) for the audio data included in the frame. 98 frames are grouped into a sector (block) and 75 such blocks constitute a unit of 1 second (i.e. audio data included in 75 continuous blocks can be played in 1 second). Each byte (8 bits) of the original frame is finally encoded in the form of 17-bit channel words and stored on the disc.

The preceding description provides an explanation of standards for CDs and CD-Rs onto which audio data is recorded. It will be appreciated that similar standards exist for optical discs onto which DVD or Blu-ray video data is recorded. Such standards are known to those skilled in the art and are not reproduced here. Any of these standards or any other similar standard may be used in various embodiments of the invention. Furthermore, it is not necessary that the data recorded on the optical disc conform to any particular standard, provided that the data recorded onto the optical disc incorporates error-detecting redundancies, the data decoding software can detect errors when the optical drive reads the recorded data and that the error mapping software can trace any detected errors to particular locations on the optical disc.

Further Discussion

The technology described herein for assessing the results of disc-based bioassays with standard optical drives allows bioassays to be prepared and their results to be assessed by non-specialists, since the methods require no modification to the optical drive, the surface chemistry involves relatively simple and mild reactions that can be carried out safely. In addition, since the measured error densities and ODRs are repeatably consistent, these quantities can be used for the construction of calibration curves to quantify analyte concentrations, which represents an advantage over prior art colorimetric diagnostic kits which are useful for qualitative (positive or negative) assessments only.

The results obtained for the experiment #2 DNA hybridization (FIGS. 5A and 5B) and for the experiment #4 IgG/anti-IgG interaction (FIGS. 7A and 7B) show results that are more sensitive than traditional fluorescence labelling/scanning. In addition, the dynamic range for each assay can be manipulated. For example, if the signal upon incubation in the target solution is strong, the silver treatment time (step 22B of FIG. 2A) can be reduced, and vice versa. Thus, the target concentration detection range can actually be made to be wider than the experimental results described herein.

With respect to signal throughput, each byte of data stored on an optical disc could be utilized for a bioassay test site. The inventors have currently successfully tested spot sizes on the order of ~260 μm for optical discs recorded with CD audio data which corresponds to about 100 reaction sites per audio CD. It is expected that the detectable resolution may be made smaller, but that there may be a limitation to detectable error resolution based on the size of the laser spot of the optical drive. A DVD system (with higher digital capacity and smaller detection laser spot size) is expected to have an even higher capacity of reaction sites.

While a number of exemplary aspects and embodiments have been discussed above, those of skill in the art will recognize certain modifications, permutations, additions and sub-combinations thereof. For example:

- In the embodiments described above, the PC surface of an optical disc is subjected to a combination of UV radiation and ozone to increase its activation energy. The combination of UV radiation and ozone may promote the formation of carboxylic acid (COOH) groups on the PC surface. Other techniques may be used to activate the PC surface of the optical disc. By way of non-limiting example, the PC surface of the optical disc may be treated by relatively high intensity UV radiation (e.g. greater than 50 mW/cm2) for a relatively long period of time without using ozone and/or the PC surface of the optical disc may be coated with a thin layer of a suitable material that is relatively active.
- In some embodiments, the UV radiation used to activate the PC surface of an optical disc may be applied to the optical disc through a mask to provide a particular pattern of activated regions on the PC surface. Masking procedures of this type are described in the Surface Activation Application. Patterns of activated regions may be used to locate particular bioassay test sites (e.g. to immobilize probe biomolecules at particular locations on the disc). For example, if the PC surface of an optical disc is activated in accordance with a particular pattern, then probe biomolecules may be spread over non-specific locations on the PC surface (e.g. without the use of fluidic plates or similar devices to located assay test sites). Since only a particular pattern of regions on the PC surface is activated, the probe biomolecules will only be immobilized in the pattern of activated regions. In still other embodiments, inkjet printing techniques may be used to selectively apply probe and target biomolecules to the surface of an optical disc.
- The embodiments described above include techniques for processing bioassays to promote signal enhancement from the optical drive by increasing the size of the positive bioassay results or by changing the color of the positive bioassay results. Both of these processes (increasing the size and changing the color) influence the laser light of the optical drive that is reflected from the optical disc in the region of the positive assay results and thereby contribute to errors in the digital data read from the optical disc. In other embodiments, different processing procedures may be undertaken to influence the optical properties of the light reflected from the optical disc in the region of the of the positive assay results. By way of non-limiting example, such procedures could cause light to be absorbed, reflected, diffracted and/or scattered from the region of the of the positive assay results or may alter the wavelength, energy or polarization of light impinging on the region of the of the positive assay results.
- The bioassay preparation procedures of block 14 could be used to monitor bioassay results using other optical devices, such as optical scanners or the like. For example, if the increase in size of the positive assay result sites resulting from the sub-block 22 processing is sufficiently large, the positive assay results may be detected by an optical scanner or other similar optical devices.

In the above-described embodiments, target biomolecules are labeled and then undergo processing, so as to increase the size of, or change the color in a vicinity of, the sites associated with positive assay results such that these positive assay results generate errors when read in an optical drive. In other embodiments, the immobilized probe biomolecules could be similarly labeled and processed, such that the sites associated with negative assay results generate errors when read in an optical drive.

In some of the embodiments described above, a threshold error density or number of errors is used in block 16 to conclude that particular detected errors correspond to positive assay results. In addition to or in the alternative to using threshold levels, in other embodiments, the error detection and mapping processes of sub-blocks 24, 26 may be performed after preparing the bioassay (sub-block 20) but before processing the bioassay (sub-block 22) to determine a background error level, in which case any error level for a particular disc location that is greater than the background error level for that disc location may be determined to correspond to a positive assay result. In some embodiments, the difference in error level relative to the background error level may also be subjected to a threshold process.

Accordingly, the invention should be interpreted in accordance with the following claims.

What is claimed is:

1. A method for assessing results of a bioassay between probe biomolecules and target biomolecules using a conventional optical disc drive, the method comprising:
    bonding the probe biomolecules to a polycarbonate (PC) surface of an optical disc having digital data comprising error-detection redundancies recorded thereon;
    introducing the target biomolecules to the PC surface of the optical disc in a vicinity of the bonded probe biomolecules;
    processing the bioassay to alter a manner in which a read light from the optical disc drive interacts optically with the optical disc in a vicinity of positive bioassay results where the target biomolecules have bonded to the probe biomolecules;
    reading the digital data from the optical disc using the optical drive and using the error-detection redundancies to detect errors in the digital data read by the optical drive;
    mapping the detected errors to corresponding locations on the optical disc; and
    determining that positive bioassay results have occurred at the locations of the detected errors.

2. A method according to claim 1 wherein the optical disc drive comprises standard unmodified optical disc drive hardware.

3. A method according to claim 1 wherein processing the bioassay comprises increasing a size of the positive bioassay results to thereby substantially alter an amount of the read light from the optical disc drive that is scattered by the positive bioassay results.

4. A method according to claim 3 wherein increasing the size of the positive bioassay results comprises an autometallography process.

5. A method according to claim 3 wherein increasing the size of the positive bioassay results comprises:
    bonding a labeling substance to the target biomolecules;
    introducing a bonding substance to the PC surface, the bonding substance comprising a conjugate of a first material bondable to the labeling substance and a seed; and
    introducing a size-increasing substance to the PC surface, the size-increasing substance bondable to the seed;
    wherein the first material of the bonding substance bonds to the labeling substance at sites of the positive bioassay results and the size-increasing substance bonds to the seed of the bonding substance to increase the size of the positive bioassay results.

6. A method according to claim 5 wherein the labeling substance comprises biotin.

7. A method according to claim 6 wherein bonding the labeling substance to the target biomolecules occurs prior to introducing the target biomolecules to the PC surface of the optical disc.

8. A method according to claim 5 wherein the first material of the bonding substance comprises an anti-biotin antibody.

9. A method according to claim 5 wherein the first material of the bonding substance comprises streptavidin.

10. A method according to claim 5 wherein the target biomolecules each comprise a protein and the labeling substance comprises an antibody of the protein.

11. A method according to claim 10 wherein bonding the labeling substance to the target biomolecules occurs after introducing the target biomolecules to the PC surface of the optical disc.

12. A method according to claim 10 wherein bonding the labeling substance to the target biomolecules comprises bonding the antibody to the protein at a bonding site different than a bonding site where the target molecule is bonded to the probe biomolecule.

13. A method according to claim 10 wherein the labeling substance comprises biotin.

14. A method according to claim 13 wherein the first material of the bonding substance comprises an anti-biotin antibody.

15. A method according to claim 13 wherein the first material of the bonding substance comprises streptavidin.

16. A method according to claim 5 wherein the seed of the bonding substance comprises a stable metal nanoparticle.

17. A method according to claim 5 wherein the seed of the bonding substance comprises a gold nanoparticle.

18. A method according to claim 5 wherein the size-increasing substance comprises stable metal nanoparticles.

19. A method according to claim 5 wherein the size-increasing substance comprises silver nanoparticles.

20. A method according to claim 3 wherein increasing the size of the positive bioassay results comprises:
    bonding a labeling substance to the target biomolecules;
    introducing a bonding substance to the PC surface, the bonding substance comprising a seed bondable to the labeling substance; and
    introducing a size-increasing substance to the PC surface, the size-increasing substance bondable to the seed;
    wherein the seed of the bonding substance bonds to the labeling substance at sites of the positive bioassay results and the size-increasing substance bonds to the seed of the bonding substance to increase the size of the positive bioassay results.

21. A method according to claim 20 wherein the labeling substance comprises a thiol (—SH) group.

22. A method according to claim 20 wherein the target biomolecules each comprise a protein and the labeling substance comprises an antibody of the protein.

23. A method according to claim 22 wherein bonding the labeling substance to the target biomolecules occurs after introducing the target biomolecules to the PC surface of the optical disc.

24. A method according to claim 22 and wherein bonding the labeling substance to the target biomolecules comprises bonding the antibody to the protein at a bonding site different than a bonding site where the target molecule is bonded to the probe biomolecule.

25. A method according to claim 20 wherein the seed of the bonding substance comprises a stable metal nanoparticle.

26. A method according to claim 20 wherein the seed of the bonding substance comprises a gold nanoparticle.

27. A method according to claim 20 wherein the size-increasing substance comprises stable metal nanoparticles.

28. A method according to claim 20 wherein the size-increasing substance comprises silver nanoparticles.

29. A method according to claim 3 wherein increasing the size of the positive bioassay results comprises:
  bonding a labeling substance to the target biomolecules, the labeling substance comprising a seed; and
  introducing a size-increasing substance to the PC surface, the size-increasing substance bondable to the seed;
  wherein the size-increasing substance bonds to the seed to increase the size of the positive bioassay results.

30. A method according to claim 29 wherein the labeling substance comprises a thiol (—SH) group.

31. A method according to any one of claim 29 wherein the target biomolecules each comprise a protein and the labeling substance comprises an antibody of the protein.

32. A method according to claim 31 wherein bonding the labeling substance to the target biomolecules occurs after introducing the target biomolecules to the PC surface of the optical disc.

33. A method according to claim 31 and wherein bonding the labeling substance to the target biomolecules comprises bonding the antibody to the protein at a bonding site different than a bonding site where the target molecule is bonded to the probe biomolecule.

34. A method according to claim 29 wherein the seed of the bonding substance comprises a stable metal nanoparticle.

35. A method according to claim 29 wherein the seed of the bonding substance comprises a gold nanoparticle.

36. A method according to claim 29 wherein the size-increasing substance comprises stable metal nanoparticles.

37. A method according to claim 29 wherein the size-increasing substance comprises silver nanoparticles.

38. A method according to claim 1 wherein processing the bioassay comprises selectively locating a colored material in a vicinity of the positive bioassay results to thereby substantially alter an amount of the read light from the optical disc drive that is absorbed in the vicinity of the positive bioassay results.

39. A method according to claim 38 wherein selectively locating a colored material in a vicinity of the positive bioassay results comprises introducing a color-changing material to the PC surface and selectively effecting a color-change reaction in the vicinity of the positive bioassay results.

40. A method according to claim 39 wherein effecting a color-change reaction in the vicinity of the positive bioassay results comprises effecting an enzymatic reaction-induced color change.

41. A method according to claim 39 wherein effecting a color-change reaction in the vicinity of the positive bioassay results comprises:
  bonding a labeling substance to the target biomolecules;
  introducing a bonding substance to the PC surface, the bonding substance comprising a conjugate of a first material bondable to the labeling substance and an enzyme; and
  introducing one or more color-changing reactants to the PC surface;
  wherein the first material of the bonding substance bonds to the labeling substance at sites of the positive bioassay results and the color-changing reactants undergo a color-changing reaction catalyzed by the enzyme to generate one or more reaction products in the vicinity of the positive bioassay results, the one or more reaction products having a different color than the color-changing reactants.

42. A method according to claim 41 wherein the labeling substance comprises biotin.

43. A method according to claim 42 wherein bonding the labeling substance to the target biomolecules occurs prior to introducing the target biomolecules to the PC surface of the optical disc.

44. A method according to claim 41 wherein the first material of the bonding substance comprises an anti-biotin antibody.

45. A method according to claim 41 wherein the first material of the bonding substance comprises streptavidin.

46. A method according to claim 41 wherein the target biomolecules each comprise a protein and the labeling substance comprises an antibody of the protein.

47. A method according to claim 46 wherein bonding the labeling substance to the target biomolecules occurs after introducing the target biomolecules to the PC surface of the optical disc.

48. A method according to claim 46 wherein bonding the labeling substance to the target biomolecules comprises bonding the antibody to the protein at a bonding site different than a bonding site where the target molecule is bonded to the probe biomolecule.

49. A method according to claim 46 wherein the labeling substance comprises biotin.

50. A method according to claim 49 wherein the first material of the bonding substance comprises an anti-biotin antibody.

51. A method according to claim 49 wherein the first material of the bonding substance comprises streptavidin.

52. A method according to claim 39 wherein effecting a color-change reaction in the vicinity of the positive bioassay results comprises:
  bonding a labeling substance to the target biomolecules, the labeling substance comprising an enzyme; and
  introducing one or more color-changing reactants to the PC surface;
  wherein the color-changing reactants undergo a color-changing reaction catalyzed by the enzyme to generate one or more reaction products in the vicinity of the positive bioassay results, the one or more reaction products having a different color than the color-changing reactants.

53. A method according to claim 52 wherein the target biomolecules each comprise a protein and the labeling substance comprises an antibody of the protein.

54. A method according to claim 53 wherein bonding the labeling substance to the target biomolecules occurs after introducing the target biomolecules to the PC surface of the optical disc.

55. A method according to claim 53 wherein bonding the labeling substance to the target biomolecules comprises bonding the antibody to the protein at a bonding site different than a bonding site where the target molecule is bonded to the probe biomolecule.

56. A method according to claim 41 wherein the enzyme comprises horseradish peroxidase (HRP).

57. A method according to claim 41 wherein the one or more color-changing reactants comprise tetramethylbenzidine (TMB) and hydrogen peroxide ($H_2O_2$).

58. A method according to claim 41 wherein the color-changing reaction catalyzed by the enzyme comprises an oxidation reaction.

59. A method according to claim 1 wherein determining that positive bioassay results have occurred at the locations of the detected errors comprises subjecting a density of detected errors to a threshold test and concluding that positive bioassay results have occurred at the locations where the density of detected errors is greater than a threshold.

60. A method according to claim 1 wherein the digital data comprising error-detection redundancies comprises one or more of: CD audio data; DVD video data; and Blu-ray video data.

61. A method according to claim 60 wherein mapping the detected errors to corresponding locations on the optical disc comprises determining a playtime of the detected errors and using the playtime to determine the corresponding locations on the optical disc.

62. A method according to claim 61 wherein using the playtime to determine the corresponding locations on the optical disc comprises, for a particular playtime (t), determining the corresponding radial location (r) on the optical disc according to:

$$\frac{t}{\tau} = \frac{r^2 - r_o^2}{r_p^2 - r_0^2}$$

where:
$r_o$ is a radius of a non-programmable central region of the disc;
$r_p$ is a radius of the programmable region of the disc; and
$\tau$ is a total recordable time of the disc.

63. A method according to claim 1 the error-detection redundancies are encoded according to any one or more of: a data repetition scheme, a data parity scheme, a data checksum scheme, a cyclic redundancy check scheme, a horizontal redundancy check scheme, a vertical redundancy check scheme, a hamming distance-based scheme, a hash function scheme, a polarity scheme and a cryptographic message-based scheme.

64. A method according to claim 1 wherein bonding the probe biomolecules to the polycarbonate (PC) surface of the optical disc, introducing the target biomolecules to the PC surface of the optical disc and processing the bioassay to alter a manner in which a read light from the optical disc drive interacts optically with the optical disc in a vicinity of positive bioassay results does not significantly impact the ability to read the digital data from the optical disc using the optical drive in regions of the disc spaced apart from the vicinity of positive bioassay results.

65. A method according to claim 1 wherein reading the digital data from the optical disc using the optical drive and using the error detection redundancies to detect errors in the digital data comprises detecting an error density that is a factor of 10 or more greater in the vicinity of positive bioassay results than an error density in regions spaced apart from the vicinity of positive bioassay results.

66. A method for using a conventional optical disc drive to assess results of a bioassay between probe biomolecules bonded to a polycarbonate (PC) surface of an optical disc having digital data comprising error detecting redundancies recorded thereon and target biomolecules, the method comprising:
processing the bioassay to alter a manner in which a read light from the optical disc drive interacts optically with the optical disc in a vicinity of positive bioassay results where the target biomolecules have bonded to the probe biomolecules;
reading the digital data from the optical disc using the optical drive and using the error-detection redundancies to detect errors in the digital data read by the optical drive;
mapping the detected errors to corresponding locations on the optical disc; and
determining that positive bioassay results have occurred at the locations of the detected errors.

67. A method according to claim 66 wherein the optical disc drive comprises standard unmodified optical disc drive hardware.

68. A method according to claim 66 wherein processing the bioassay comprises increasing a size of the positive bioassay results to thereby substantially alter an amount of the read light from the optical disc drive that is scattered by the positive bioassay results.

69. A method according to claim 68 wherein increasing the size of the positive bioassay results comprises an autometallography process.

70. A method according to claim 66 wherein processing the bioassay comprises selectively locating a colored material in a vicinity of the positive bioassay results to thereby substantially alter an amount of the read light from the optical disc drive that is absorbed in the vicinity of the positive bioassay results.

71. A method according to claim 70 wherein selectively locating a colored material in a vicinity of the positive bioassay results comprises introducing a color-changing material to the PC surface and selectively effecting a color-change reaction in the vicinity of the positive bioassay results.

72. A method according to claim 71 wherein effecting a color-change reaction in the vicinity of the positive bioassay results comprises effecting an enzymatic reaction-induced color change.

73. A system for assessing results of a bioassay between probe biomolecules bonded to a polycarbonate (PC) surface of an optical disc having digital data comprising error detecting redundancies recorded thereon and target biomolecules, the system comprising:
a conventional optical disc drive configured to read the digital data from the optical disc;
a bioassay processor for processing the bioassay to alter a manner in which a read light from the optical disc drive interacts optically with the optical disc in a vicinity of positive bioassay results where the target biomolecules have bonded to the probe biomolecules; and
a computer connected to receive the digital data read by the optical drive and configured to:
use the error-detection redundancies to detect errors in the digital data read by the optical drive;
map the detected errors to corresponding locations on the optical disc; and
determine that positive bioassay results have occurred at the locations of the detected errors.

* * * * *